(12) United States Patent
Reese et al.

(10) Patent No.: US 11,254,924 B2
(45) Date of Patent: Feb. 22, 2022

(54) METHOD FOR BIOCATALYSIS USING FILAMENTOUS FUNGI

(75) Inventors: Paul B. Reese, Kingston (JM); Patrice Peart, Portland (JM); Avril R. M. Chen-Collins, St. James (JM)

(73) Assignee: The University of The West Indies, Kingston (JM)

( * ) Notice: Subject to any disclaimer, the term of this patent is extended or adjusted under 35 U.S.C. 154(b) by 1382 days.

(21) Appl. No.: 12/390,079

(22) Filed: Feb. 20, 2009

(65) Prior Publication Data
US 2009/0246850 A1 Oct. 1, 2009

Related U.S. Application Data

(60) Provisional application No. 61/029,957, filed on Feb. 20, 2008.

(51) Int. Cl.
| | | |
|---|---|---|
| C12N 11/04 | (2006.01) |
| C12P 33/00 | (2006.01) |
| C12P 33/06 | (2006.01) |
| C12P 39/00 | (2006.01) |
| C12P 33/08 | (2006.01) |

(52) U.S. Cl.
CPC .............. *C12N 11/04* (2013.01); *C12P 33/00* (2013.01); *C12P 33/06* (2013.01); *C12P 33/08* (2013.01); *C12P 39/00* (2013.01)

(58) Field of Classification Search
None
See application file for complete search history.

(56) References Cited

U.S. PATENT DOCUMENTS

| | | | |
|---|---|---|---|
| 4,718,935 | A | 1/1988 | Walker et al. |
| 5,766,907 | A | 6/1998 | Chang et al. |
| 6,153,416 | A | 11/2000 | Yuan |
| 6,204,049 | B1 | 3/2001 | Bennett et al. |
| 2003/0165472 | A1 | 9/2003 | McGrath et al. |

FOREIGN PATENT DOCUMENTS

WO WO-9820151 A1 * 5/1998 ............ C07J 5/0053

OTHER PUBLICATIONS

Holland et al. (Effect of cell immobilization and organic solvents on sulfoxidation and steroid hydroxylation by Mortierella isabellina, 1992, Journal of Industrial Microbiology).*
Larroche et al. (Special transformation processes using fungal spores and immobilized cells, 1997, Advances in Chemical Engineering/Biotechnology, vol. 55, pp. 179-220).*
Lamm et al. (Bioconversion of Stemodia maritima diterpenes and derivatives by *Cunninghamella echinulata* var. elegans and Phanerochaete chrysosporium, 2006, Phytochemistry, vol. 67, pp. 1088-1093).*
Agrawal et al. (Bioconversion of alpha pinene to verbenone by resting cells of Aspergillus niger, 2000, Applied Microbiology and Biotechnology, vol. 53, pp. 335-337).*
Sonomoto et al. (11a-hydroxylation of progesterone by gel-entrapped living Rhizopus stolonifera mycelia, 1982, Eur J Appl Microbiol Biotechnol, vol. 16, pp. 57-62).*
Mona Chemistry list, Chemistry Thesis list, 2017.*
Mazumder, Sequential conversion of cortexolone to prednisolone by immobilized mycelia of Curvularia lunata and immobilized cells of Arthrobacter simplex, Appl Microbiol Biotechnol (1985) 21 : 154-161.*
Ghanem et al., Transformation of Reichstein's Compound S into Prednisolone by Immobilized Mixed Cultures, J. Chem. Tech. Biotechnol. 1992, 54, 115-121.*
Ghanem, Khaled M., Samy A. El-Aassar, and Hoda H. Yusef. "Transformation of Reichstein's compound S into prednisolone by immobilized mixed cultures." Journal of Chemical Technology & Biotechnology 54.2 (1992): 115-121. (Year: 1992).*
Manosroi, J., Y. Chisti, and A. Manosroi. "Biotransformation of cortexolone to hydrocortisone by molds using a rapid color-development assay." Applied Biochemistry and Microbiology 42.5 (2006): 479-483. (Year: 2006).*
Ohlson, Sten, et al. "Steroid hydroxylation using immobilized spores of Curvularia lunata germinated in situ." European journal of applied microbiology and biotechnology 10.1-2 (1980): 1-9. (Year: 1980).*
Auret, "Microbiological 18-Hydroxylation of Steroids", J. Chem. Soc. Chem. Comm., 1157 (1971).
Belan, et al., "Use of Biological Systems for the Preparation of Chiral Molecules. 3. An Application in Pheromone Synthesis: Preparation of Sulcatol Enantiomers", J. Org. Chem., 52:256-260(1987).
Canonica et al.,"The Microbiological Oxidation of INsect Moulting Hormones", J. Chem. Soc. Chem. Comm., pp. 656-657 (1974).
Eppstein, et al., "Microbiological Transformations of Steroids. X. The Oxygenation of Androgens by Rhizopus", J. Chem. Soc., 76:3174-3179 (1954).
European Search Report issued for EP 06 15 3322, dated Apr. 29, 2009 (2 pages).
Garcia-Rodriguez, et al., "Microbiological Hydroxylation of Steroids, IV. Influence of Thermal Treatment on the Enzyme Activity of Hydroxylating Cultures", translation of Khimiko-Farmatsevticheskii Zhurnal, 15(10):73-75 (1981).
Garcia-Rodriguez, et al., "Microbiological Hydroxylation of Steroids. III. Study of Side Reactions Occurring in the Hydroxylation of Cortexolone in Cultures of *Cunningamella blakesleeana* and *Curvularia lunata*", translated from Khimiko-Farmatsevticheskii Zhurnal, 12(9):95-97 (1978).
Holland, "Microbial Hydroxylation of Steroids. 8. Incubation of Cn halo- and Other Substituted Steroids with Cn Hydroxylating Fungi", Can. J. Chem., 60(2):160-164 (1982).
Holland, et al., "Microbial Hydroxylation of Steroidal Δ3,5 Enol Acetates", Tetrahedron Lett., 44:3787-3788 (1975).

(Continued)

Primary Examiner — Robert J Yamasaki
(74) Attorney, Agent, or Firm — Wilmer Cutler Pickering Hale and Dorr LLP

(57) ABSTRACT

A method is disclosed in which filamentous fungi are macerated and encapsulated in an inert matrix to form beads, which can be used to promote reactions carried out by the fungi. The beads are useful, e.g., for producing compounds and compound libraries.

9 Claims, No Drawings

(56) References Cited

OTHER PUBLICATIONS

Holland, et al., "The Mechanism of the Microbial Hydroxylation of Steroids. Part 1. The C-21 Hydroxylation of Progesterone by Aspergillus niger ATCC 942", Can. J. Chem., 53:845-854 (1975).

Hufford, et al., "Preparation, Characterization, and Antiviral Activity of Microbial Metabolites of Stemodin", J. Nat. Prod., 54(6):1543-1552 (1991).

Kaneko, "Microbial Transformation of Steroid. I. Mocrobiological Hydroxylation of Diosgenin", Chem. Pharm. Bull. Jpn., 17(10):2031-2035 (1969).

Lacroix, et al., "Microbial Models of Drug Metabolism: Microbial Transformations of Trimegestone® (RU27987), a 3-Keto-Δ4,9(10)-19-norsteroid Drug", Bioorg. Med. Chem., 7:2329-2341 (1999).

Lamm, et al., "Steroid Hydroxylation by Whetzelinia Sclerotiorum, Phanerochaete Chrysosporium and Mucor Plumbeus", Steroids, 72(9-10):713-722 (2007) (10 pages).

Maddox, et al., "Use of Immobilized Cells of Rhizopus-Nigricans for the 11-Alpha Hydroxylation of Progesterone", Biotechnology and Bioengineering, 23(2):345-354 (1981) (10 Pages).

O'Reilly, et al., "Defined Coimmobilization of Mixed Microorganism Cultures", Enzyme Microb. Technol., 17:636-646 (1995).

Pearson, et al., "A New Method for the Oxidation of Alkenese to Enones. An Efficient Synthesis of Δ5-7-Oxo Steroids", J. Chem. Soc. Perkin Trans., 1:267-273 (1985).

Peterson, et al., "Microbiological Transformations of Steroids. I. Introduction of Oxygen at Carbon-11 of Progesterone", J. Am. Chem. Soc., 74:5933-5936 (1952).

Roy, et al., "Use of Immobilized Biocatalysts in Fluidized Red Format", Methods in Biotechnology, Humana Press, Inc., Totowa, NJ, pp. 311-319 (2006) (11 Pages).

Wilson, et al., "Steroid Transformations with *Fusarium oxysporum* var. *cubense* and *Collectotrichum musae*", Steroids, 64:834-843 (1999).

Yamashita, et al., "Microbial 16 β-Hydroxylation of Steroids with Aspergillus niger", Agric. Biol. Chem., 40:505-509 (1976).

Adinarayana, et al., "Production of Alkaline Protease With Immobilized Cells of Bacillus subtilis PE-11 in Various Matrices by Entrapment Technique", AAPS PharmSciTech 2006, 6(3) Article 48, pp. E391-E397.

Chen, "Chapter 6: Biotransformation of Steroids Using Free and Immobilised Fungal Cells", Thesis, 2001, 61 pages.

McCabe, et al., "Immobilization of Monocentric and Polycentric Types of Anaerobic Chytrid Fungi in Ca-alginate", Enzyme and Microbial Technology, vol. 29, 2001, pp. 144-149.

Ramakrishna, et al., "Microbial Fermentations with Immobilized cells", Biochemical and Environmental Engineering, Indian Institute of Chemical Technology, Hyderabad 500 007, India, www.ias.ac.in/currsci/jul10/articles17.htm, Accessed Jan. 10, 2008, 22 pages.

\* cited by examiner

METHOD FOR BIOCATALYSIS USING FILAMENTOUS FUNGI

CROSS-REFERENCE TO RELATED APPLICATIONS

This application claims the benefit of priority under 35 U.S.C. § 119(e) to U.S. Application No. 61/029,957, filed on Feb. 20, 2008, entitled "Method for Biocatalysis Using Filamentous Fungi," which is incorporated herein by reference in its entirety.

TECHNICAL FIELD

This application relates to the field of biocatalysis.

BACKGROUND

Biocatalysis is an area of growing importance in the field of organic synthesis where there is great potential for the generation of biologically active molecules. Microorganisms and their enzymes are both exploited in laboratory and industrial transformations. Nevertheless, these bioconversions provide certain challenges. Transformed products often need to be purified from microbial natural products; there is a great need for sterility; and, generally, the cells are not reusable once the fermentation is complete.

Filamentous fungi are fungi that grow in long multi-cell strands (hyphae). The mycelium is a mass formed by hyphae. Some fungi have the ability to switch between a cellular form and a filamentous form in response to environmental cues. For example, the human pathogen *Candida albicans* and the corn smut fungus *Ustilago maydis* can effect such a change.

SUMMARY

It has been found that filamentous fungi can be immobilized in a matrix and used for biocatalysis. The immobilized fungi can be used in multiple reactions, can be stored in simple solutions including water, and do not require complex media for maintenance. In particular, mature mycelia can be used. Accordingly, the invention includes a method of immobilizing a filamentous fungus in a matrix. The method includes providing a filamentous fungus; macerating the filamentous fungus, thereby providing a macerated sample; suspending the macerated sample in aqueous sodium alginate, thereby providing a fungal sodium alginate sample; adding the fungal sodium alginate sample to a calcium chloride solution, thereby forming fungal alginate beads; and isolating fungal alginate beads.

The invention also relates to a bead that includes a filamentous fungus and an inert matrix. In some cases, the inert matrix includes calcium alginate. In some embodiments, the fungus is *Rhizopus oryzae, Mucor plumbeus, Cunninghamella echinulata, Aspergillus niger, Phanerochaete chrysosporium,* or *Whetzelinia sclerotiorum.*

In another aspect, the invention relates to a method of producing one or more compounds using bioconversion. The method includes providing a bead that includes a filamentous fungus and an inert matrix; contacting the bead with a compound that can be metabolized by the filamentous fungus, thereby producing a metabolite sample; incubating the metabolite sample under conditions suitable for metabolism of the compound by the filamentous fungus, thereby producing a bioconversion compound. In some embodiments, the method also includes isolating at least one product from the incubated metabolite sample. The compound used in the method can be, for example, a steroid. In certain embodiments, at least two beads each comprising a different filamentous fungus, are used in the method.

The invention also relates to a method of producing a library of bioconversion compounds. The method includes providing a first fungal bead containing a first fungal species and providing a second fungal bead containing a second fungal species; combining the beads in a single vessel; contacting the beads in the vessel with a compound, thereby forming an incubation mixture; incubating the incubation mixture under conditions and for a time sufficient to produce bioconversion, thereby producing a library of bioconversion compounds. In some embodiments, the compound is a steroid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DETAILED DESCRIPTION

Filamentous fungi are an important current and potential source of useful molecules. The present invention provides methods of capturing mycelia of filamentous fungi in a matrix in which the fungal cells remain viable and retain their ability to perform biotransformations on exogenous substrates. Such a matrix containing a filamentous fungus is termed herein a "fungal bead." Fungal beads can be used for synthesis of libraries of fungal metabolites, for example, by incubating the beads with one or more selected substrates such as steroid compounds and recovering the products of the incubation that are generated via biocatalysis. Libraries of fungal metabolites are useful, e.g., as a source of new compounds having therapeutic or other commercial potential.

The advantages of using fungal beads as described herein include (i) Formation of transformed compounds, similar to those compounds formed under normal fermentation conditions, i.e., fermentation conditions using free cells.

(ii) The incorporation of the fungi into beads facilitates separation of fungi from medium compared to separating fungal filaments from media. This greatly reduces work up time and results in a cleaner initial preparation of products, thus facilitating isolation of products.

(iii) Because the fungal cells do not grow, or do not grow significantly within the beads, the cells do not require the addition of nutrients during the fermentation process used for production of compounds.

(iv) The fungi in beads do not produce significant amounts of natural products. Therefore, there is little or no need to separate transformed compounds from any secondary metabolites produced by the fungi that are not derived from the compound being transformed.

(v) When a fermentation using fungal beads is completed, the used beads can be resuspended in water and stored in the refrigerator. The beads can be re-used in subsequent fermentations.

(vi) Although, for the most part, the products of biocatalysis from the bead experiment parallel those from the liquid culture run, sometimes new products are generated in the former as well.

(vii) The fungal bead method can be used for producing metabolites from filamentous fungi that do not produce spores.

Fungi for Use in Preparation of Fungal Beads

Any type of filamentous fungus can be used to prepare fungal beads. This includes fungi that form mycelia only under certain conditions as is the case with some pathogenic fungi.

Specific, non-limiting examples of filamentous fungi suitable for incorporation into fungal beads include *Rhizopus oryzae* (e.g., ATCC 11145), *Mucor plumbeus* (e.g., ATCC 4740), *Cunninghamella echinulata* var. *elegans* (e.g., ATCC 8688a), *Aspergillus niger* (e.g., ATCC 9142), *Phanerochaete chrysosporium* (e.g., ATCC 24725), and *Whetzelinia sclerotiorum* (e.g., ATCC 18687).

To prepare fungi for incorporation into a fungal bead the fungi are cultured, for example, using methods suitable for culturing (fermenting) the fungus that are known in the art. Typically, a culture of a selected filamentous fungus is grown in a suitable culture medium, harvested, and resuspended, for example, resuspended in water. The fungal culture is typically harvested in log phase, although it can be harvested in stationary phase.

Preparation of Fungal Beads

Fungal beads are prepared using filamentous fungi, e.g., prepared as described supra. Typically, the fungal cells are resuspended in distilled water. A sodium alginate solution is added to the cells to bring the sodium alginate concentration to about 2.33%. The cells in sodium alginate are then macerated such that there is relatively little cell breakage and mycelia are disrupted, e.g., at least some cells are present as single cells, although it is not necessary that all cells be present as single cells. An example of suitable maceration conditions is maceration using an IKA® Ultra-Turrax® T25 homogenizer at 8,000 rev/minute for about 30 seconds to 10 minutes, e.g., for 2 minutes, 3 minutes, 4 minutes, 5 minutes, or 7 minutes. Maceration conditions can be adapted to different types of fungi or different types of homogenizers using the conditions provided herein for guidance. Suitable maceration conditions are identified by testing activity of beads formed using fungi prepared using various maceration conditions.

The resulting suspension of cells in sodium alginate is then added dropwise to cold (e.g., about 4° C.) 0.1 M calcium chloride with stirring to form beads. Bead size can be modulated by selecting the bore size of the dropper. Beads are allowed to harden in the solution, e.g., for about 30 minutes, after which they are rinsed and stored in distilled water or other suitable aqueous solution at 4° C.

In general, beads are stored in water, although they can be stored in a buffer.

Other methods known in the art can be used to form beads. In non-limiting examples, beads can be made of nylon, proteins such as collagen, carbohydrates (e.g., carrageenan, agarose), or other polymeric materials (e.g., polyacrylamide, polyurethane). In general, the calcium alginate method is relatively easy to execute and is therefore used in the examples provided herein.

Fermentation Reactions and Metabolites

To produce compounds by biocatalysis using immobilized filamentous fungi, i.e., filamentous fungi in fungal beads, the beads are incubated with a selected compound or compounds for a suitable period of time, typically about 1 day-10 days, for example, 3 days, 4 days, 5 days, 6 days, 7 days, or 8 days. After incubation, the beads are collected and the incubation medium is treated to extract compounds, including those that were formed by biocatalysis during the incubation. Any type of compound that is susceptible to biotransformation by a species of filamentous fungus can be used in the methods described herein. For example, compounds that can be produced using the fungal beads described herein include steroids and derivatives of steroids, and diterpenes. These methods are particularly useful for biotransformation of compounds via hydroxylation.

After an incubation is complete, beads are separated from the incubation solution, for example, by permitting the beads to settle and recovering the incubation solution by decanting. The recovered incubation solution can then be used as a source of mixed compounds in, for example, screening assays to identify active compounds. Alternatively, compounds can be isolated from the recovered incubation solution using methods known in the art such as organic extraction and drying. Products can be analyzed and/or separated using methods known to those in the art.

In some cases, the biocatalysis reactions in the incubation are mixed cell biotransformation reactions. Mixed cell reactions are those in which fungal beads derived from at least two different types of fungi are included in the incubation.

Recycling of Fungal Beads

Surprisingly, it was found that the fungal beads generated as described herein can be reused. Typically, after using fungal beads in a biocatalysis reaction, the beads are washed, for example in distilled water or in a buffer and stored in water or a buffer under refrigeration, e.g., at about 4-5° C.

Fungal beads can be reused in a biocatalysis reaction after storage without additional treatment. However, in some cases, beads that have been used for biocatalysis are pretreated before use in additional reactions. The pretreatment can be incubation in a medium containing at least an energy source such as a culture medium suitable for culturing the filamentous fungus immobilized in the bead, for example, glucose solution, potato broth, or potato dextrose broth. In some cases, a simple solution can be used such as a glucose solution. Pretreatment of used beads can be before the beads are stored or immediately before they are reused. In general, incubation of fungal beads in an energy source prior to reuse results in increased yields of products compared to fungal beads that are not incubated in an energy source prior to reuse.

Compounds

Compounds produced by biocatalysis using fungal beads are useful, for example as known or novel steroids that have known utilities or as a source of test compounds that can be tested for activities. Biocatalysis using fungal beads can be used as a method of production for compounds that minimizes contaminants, e.g., compared to methods using free cells or chemical methods. As illustrated herein, fungal beads are useful for producing steroid compounds. However, those in the art will understand that other compounds that are susceptible to biotransformation can be used in the methods described herein to produce additional compounds.

Combinatorial Biocatalysis

The generation of chemical libraries typically involves producing a number of different compounds within a single reaction vessel. The complex mixture of compounds produced in this manner can be screened for biological activity without isolating the individual components of the mixture in initial screens. If a desired bioactivity is identified in the complex mixture, then the mixture can be subjected to separation processes and further assay to identify the specific compound(s) having the desired activity. This technique can be applied to reactions catalyzed by enzymes. However, limitations to the method are encountered when enzymes are used. In some cases suitable enzymes are difficult or impossible to isolate and purify, and stability of an enzyme in solution can be poor. In addition, costly cofactors are sometimes required in the enzymatic reactions.

Another approach to generating chemical libraries is to use intact cells in a sequential protocol. For example, cells are incubated with a selected compound, which is metabolized by the cells to yield additional compounds. The compounds from this first incubation are extracted and added to a second culture containing a second organism that is different from the first organism. Metabolites from the second reaction can be extracted and used as a chemical library. In an alternative approach to a two organism scheme for generating a chemical library, a compound is incubated in a culture in which two or more organisms are growing, thereby generating a number of metabolites that can be extracted. However, it is difficult to effectively grow multiple cell types in a single culture because the cells can adversely affect each other, for example, by competition, predation, parasitism and amensalism, which results in low yields of products (O'Reilly et al., *Enzyme Microb. Technol.*, 1995, 17, 636-646).

Mixed Cell Biotransformation

In certain aspects, the present invention relates to methods that are effective for generating products by two different organisms incubated with a compound within the same reaction vessel (mixed cell biotransformation). In general, the method includes generating fungal beads as described herein and mixing beads containing different types of fungi in the same reaction vessel with a compound to be used as a substrate for biotransformation.

Without committing to any particular theory, the effectiveness of this method is, at least in part, because a single fungal type is immobilized within a bead and therefore the cells of different types are not in close contact with each other, nor are they growing. Therefore, the fungi are producing fewer products that can inhibit fungal growth and a fungal type will not significantly affect reactions performed by other fungal types in the reaction. This method can be used to form libraries of chemical substances by incubating one or more selected single compounds (substrate) to a reaction mixture containing two or more types (e.g., 2, 3, 4, 5, or 6 types) of fungal beads, each bead type containing a different fungal species or variant fungus.

EXAMPLES

The invention is further illustrated by the following examples. The examples are provided for illustrative purposes only. They are not to be construed as limiting the scope or content of the invention in any way.

Example 1

Initial Studies

The following initial studies were designed to compare the metabolites formed by incubation of a single substrate with free and immobilized mycelia of various filamentous fungi, specifically, *Mucor plumbeus, Aspergillus niger, Rhizopus oryzae* and *Cunninghamella echinulata* var. *elegans*. The immobilized fungi were immobilized in a calcium alginate matrix to form beads.

Materials and Methods

Materials

Sodium alginate was obtained from Aldrich Chemical Company (Milwaukee, Wis., USA). 3β-Hydroxyandrost-5-en-17-one (52) was obtained from Steraloids, Inc. (Wilton, N.H., USA). *Mucor plumbeus* ATCC 4740, *Aspergillus niger* ATCC 9142, *Rhizopus oryzae* ATCC 11145 and *Cunninghamella echinulata* var. *elegans* ATCC 8688a were obtained from the American Type Culture Collection, Rockville, Md., USA and were maintained on potato dextrose agar slants.

Chromatographic Analysis

Flash column chromatography for the isolation and purification of secondary metabolites employed silica gel (230-400 mesh) or basic alumina (150 mesh). Thin layer chromatography plates were visualized under ultraviolet light or by spraying with ammonium molybdate-sulfuric acid reagent or by spraying with a mixture of methanol-concentrated sulfuric acid (1:1) and heating. Polyester backed TLC plates coated with silica were used for these analyses.

Instrumentation

Melting points were recorded on a Thomas Hoover melting point apparatus (Thomas Scientific, Swedesboro, N.J.) and are uncorrected. Infrared (IR) spectra were recorded as KBr disks using a PerkinElmer FT Paragon 1000 spectrophotometer. Optical rotations were acquired on a Perkin Elmer 241 MC polarimeter. Ultraviolet spectra were recorded on a Hewlett Packard HP 8452A diode array spectrophotometer.

Fungal mycelium was macerated at 8000 rev/min using an IKA® (Wilmington, N.C., USA) Ultra-Turrax® T25 homogenizer.

$^1$H and $^{13}$C NMR spectra were recorded using Bruker Avance 200 and 500 MHz and a Varian Unity 500 MHz spectrometers. NMR samples were analyzed in $CDCl_3$ containing tetramethylsilane as the internal standard.

High resolution mass spectroscopy (HRMS) electron ionization (EI) was done on a Kratos MS50 instrument at an ionizing voltage of 70 eV. Electrospray mass spectroscopy (ESMS) was done on an Agilent Technologies 1100 MSD or a Micromass Zabspec-oaTOF spectrometer.

Preparation of Reagents

Ammonium molybdate-sulfuric acid spray was prepared by dissolving ammonium molybdate (5% w:v) in a 10% sulfuric acid solution.

Methanol-sulfuric acid spray was prepared by slowly adding an equal volume of sulfuric acid to ice-cold methanol with stirring.

Growth Conditions

In general, fungi were cultured in media known to be suitable for growth of the selected species of fungus.

*Mucor plumbeus* was maintained on potato dextrose agar (PDA) slants at 28° C. Two week old slants were used to inoculate twenty 500 mL erlenmeyer flasks each containing 125 mL liquid culture medium. The *M. plumbeus* medium was comprised of, per liter, glucose (30 g), corn steep solids (5 g), $NaNO_3$ (2 g), KCl (0.5 g), $MgSO_4 \cdot 7H_2O$ (0.5 g) and $FeSO_4 \cdot 7H_2O$ (0.02 g). The flasks were shaken at 250 rpm.

*Aspergillus niger* was grown on PDA slants at 28° C. for two weeks. Five slants were used to inoculate twenty 500 mL erlenmeyer flasks, each containing 125 mL liquid culture medium. The *A. niger* medium was comprised of, per liter, glucose (20 g), yeast extract (5 g), soya meal (5 g), NaCl (5 g), and $K_2HPO_4$ (5 g) (Belan et al., *J. Org. Chem.,* 1987, 52, 256-260). The flasks were shaken at 180 rpm.

*Rhizopus arrhizus* was maintained on malt agar slants at 28° C. Two week old slants were used to inoculate twenty 500 mL erlenmeyer flasks, each containing 125 mL liquid culture medium. The *R. arrhizus* medium was comprised of, per liter, glucose (20 g), peptone (5 g), NaCl (5 g) and yeast extract (5 g) (Hufford et al., *J. Nat. Prod.,* 1991, 54, 1543-1552). The flasks were shaken at 250 rpm.

*Cunninghamella echinulata* var. *elegans* was grown on slants prepared from peptone (10 g/L), maltose (40 g/L) and agar (20 g/L) and maintained at 28° C. for two weeks. Five slants were used to inoculate twenty 500 mL erlenmeyer flasks that each contained 125 mL of liquid culture medium. The *C. echinulata* medium was contained, per liter, glucose (20 g), yeast extract (5 g), soya meal (5 g), NaCl (5 g), and $K_2HPO_4$ (5 g) (Belen et al., supra). The flasks were shaken at 180 rpm.

Preparation of Immobilized Fungal Cells

In general, to prepare cells for immobilization, one slant of a selected fungus was used to inoculate four erlenmeyer flasks each containing 125 mL growth medium. The cultures were grown for three days. At the end of incubation the cells were harvested by filtration.

The cells from one flask (about 15 g) were then suspended in water (10 mL) and then were macerated in a 3% solution of sodium alginate (35 mL). The cell-alginate suspension was added dropwise to a chilled stirred solution of 0.1 M aqueous $CaCl_2$ (200 mL). Once formed the alginate beads (about 30 g; fungal beads) were allowed to harden for 30 minutes in the $CaCl_2$ solution. The aqueous $CaCl_2$ was decanted and the beads were stored in water at 4° C.

Synthesis of
3β,17β-DIHYDROXYANDROST-5-ENE (53)

3β,17β-dihydroxyandrost-5-ene was used as a substrate in some experiments. To prepare the compound, sodium borohydryde (200 mg, 5.29 mmol) was added to 3β-hydroxyandrost-5-en-17 one (52) (1 g, 3.47 mmol) in methanol (50 mL) at 0° C. with stirring. The reaction mixture was stirred for an additional 30 minutes. Water was added and the solution was extracted with ethyl acetate. The organic layer was dried with sodium sulfate and the solvent was removed in vacuo to yield 3β,17β-dihydroxyandrost-5-ene (53) (984 mg, 3.23 mmol). This was characterized as the diacetate (53a), which crystallized from methanol as plates, m.p. 150-153°, $[\alpha]_D$–39.7° (c=3.0, $CHCl_3$), lit. (Pearson et al., *J. Chem. Soc. Perkin Trans.* 1, 1985, 267) m.p. 158-159°, $[\alpha]_D$–55.0°; IR: $\nu_{max}$ 3448, 1750, 1644, 1242 $cm^{-1}$;

$^1$H NMR: δ 0.79 (3H, s, H-18), 1.04 (3H, s, H-19), 2.04 (6H, s, 2 $CH_3CO_2$), 4.27 (1H, t, J=9.2 Hz, H-17α), 4.51 (1H, t, J=9.2 Hz, H-3α), 5.39 (1H, d, J=6.1 Hz, H-6);

$^{13}$C NMR: δ 11.9 ($CH_3$-18), 19.3 ($CH_3$-19), 20.4 ($CH_2$-11), 21.1 ($\underline{C}H_3CO_2$-3), 21.4 ($\underline{C}H_3CO_2$-17), 23.5 ($CH_2$-15), 27.5 ($CH_2$-16), 27.7 ($CH_2$-2), 31.4 ($CH_2$-7), 31.6 ($CH_2$-8), 34.4 (C-10), 36.7 ($CH_2$-12), 36.9 ($CH_2$-1), 38.0 ($CH_2$-4), 42.3 (C-13), 49.9 (CH-9), 50.9 (CH-14), 73.8 (CH-3), 82.7 (CH-17), 122.2 (CH-6), 139.7 (C-5), 170.5 ($CH_3\underline{C}O_2$-3), 171.2 ($CH_3\underline{C}O_2$-17).

Free Cell Fermentations

Fermentation Conditions

Experiments were conducted comparing free cells and cells captured in a matrix. To prepare the free cells, a solution containing 10% of the total mass of the substrate to be used in the experiment was added to the fungal culture 24 hours after inoculation. Then 20%, 30%, and 40% of the total substrate was added to the cultures at 36 hours, 48 hours, and 60 hours after inoculation respectively. The fermentation was then allowed to proceed for an additional five days. At the end of the fermentation period, the mycelial cells were filtered and the broth was extracted with ethyl acetate (3×500 mL). The mycelial cells were homogenized with hot ethyl acetate. The extracts were dried ($MgSO_4$), concentrated, and analyzed by thin layer chromatography. In general, it was found that transformed compounds were primarily present in the broth, while natural products and the fed compound were generally associated with the mycelium; although individual fungal species can be at variance with the generalization.

Bioconversions Using Free Cells

Bioconversion of
3β,17β-DIHYDROXYANDROST-5-ENE (53)

Incubation of 53 with *M. plumbeus*

Bioconversions using a selected substrate (53) were performed using free cells. The resulting products of these bioconversions were used in comparisons with bioconversions using the same fungal types immobilized in a bead to determine the equivalency of bioconversions in the bead format with free fermentations.

To examine the bioconversion of 53 *M. plumbeus*, 1 g of the compound was dissolved in ethanol (20 mL), and was added to cultures of the growing fungus as described above. Extraction of the broth and mycelia afforded an off-white solid (688.8 mg) which was purified using column chromatography. Elution of the column with 25% acetone in dichloromethane afforded unreacted steroid (52 mg). Further elution yielded 3β,7β,17β-trihydroxyandrost-5-ene (54) (610 mg), characterized as the triacetate (54a), which resisted crystallization, $[\alpha]_D$–119.9° (c=1.1, $CHCl_3$);

IR: $\nu_{max}$ 3454, 1734, 1644, 1238 $cm^{-1}$;

HREIMS: m/z (rel. int.) 372.2301 (13) $[M-AcOH]^+$ (372.2512 calcd. for $C_{25}H_{36}O_6$-AcOH), 330.21.2168 95 (51) $[M-AcOH-H_2]^+$, 313 (6), 312.2089 (9) $[M-2AcOH]^+$, 252.1878 (4) $[M-3AcOH]^+$, 159.1174 (10);

$^1$H NMR: δ 0.78 (3H, s, H-18), 1.01 (3H, s, H-19), 2.05 (9H, s, 3 $CH_3CO_2$), 2.44 (1H, t, J=9.5 Hz, H-3α), 4.62 (1H, t, J=9.5 Hz, H-17α), 4.96 (1H, t, J=7.0 Hz, H-7α), 5.57 (1H, d, J=4.7 Hz, H-6);

$^{13}$C NMR: δ 11.5 ($CH_3$-18), 18.1 ($CH_3$-19), 20.1 ($CH_2$-13), 21.1 ($CH_3CO_2$-3), 21.2 ($CH_3CO_2$-7), 21.3 ($CH_3CO_2$-17), 23.4 ($CH_2$-16), 27.3 ($CH_2$-15), 27.7 ($CH_2$-2), 35.5 (CH-8), 36.0 ($CH_2$-1), 36.4 ($CH_2$-4), 37.3 (C-10), 37.7 ($CH_2$-12), 42.1 (C-13), 43.1 (CH-14), 43.6 (CH-9), 67.5 (CH-7), 73.0 (CH-3), 82.4 (CH-17), 120.5 (CH-6), 146.6 (C-5), 170.4 ($CH_3CO_2$-3), 170.7 ($CH_3CO_2$-7), 171.2 ($CH_3CO_2$-17).

Incubation of 53 with *A. niger*

*A. niger* bioconversion was also tested using the steroid compound 53. The steroid (53) (1 g) was dissolved in ethanol (20 mL) and added to a fungal culture as described supra. The incubation period was continued for five days after the last addition of steroid. Following the incubation period, the contents of the flasks were filtered and the broth and mycelia were extracted with ethyl acetate, dried with sodium sulfate, and the solvent was removed in vacuo. This resulted in an off-white solid (1 g), which was purified using column chromatography. Elution with 25% acetone in dichloromethane produced unreacted steroid (696 mg). Further elution produced 3β,7β,17β-trihydroxyandrost-5-ene (54) (66 mg), which was identified by comparison with an authentic sample.

Bioconversion of 53 by *R. oryzae*

*R. oryzai* biocatalysis was also tested using the steroid compound (53) (1 g), which was dissolved in ethanol (20 mL), and added to the culture medium containing the growing fungus. The incubation period was continued for five days after the last feeding of the culture. The contents of the flasks were then filtered and the broth and mycelia were extracted with ethyl acetate, dried with sodium sulfate, and the solvent was removed in vacuo. This resulted in an off-white solid (1 g) that was then purified using column chromatography. Elution with 25% acetone in dichloromethane afforded unreacted steroid (632 mg). Further elution yielded 3β,7α,17β-trihydroxyandrost-5-ene (55) (106.1 mg), characterized as the triacetate (55a), gum, $[\alpha]_D$–151° (c=6.7, CHCl$_3$), lit. (Wilson et al., *Steroids*, 1999, 64, 834-843), m.p. 156-158°, $[\alpha]_D$–152';

IR: $\nu_{max}$ 3446, 1736, 1660, 1241 cm$^{-1}$;

$^1$H NMR: δ 0.82 (3H, s, H-18), 1.10 (3H, s, H-19), 2.04 (9H, s, 3 CH$_3$CO$_2$), 4.60 (1H, m, w/2=15.5 Hz, H-17α), 5.04 (1H, d, J=10.1 Hz, H-7β), 5.25 (1H, s, H-6);

$^{13}$C NMR: δ 11.8 (CH$_3$-18), 18.9 (CH$_3$-19), 20.5 (CH$_2$-11), 21.1 (CH$_3$CO$_2$-3), 21.3 (CH$_3$CO$_2$-7), 21.6 (CH$_3$ CO$_2$-17), 24.6 (CH$_2$-16), 27.1 (CH$_2$-15), 27.2 (CH$_2$-2), 36.3 (CH-8), 36.5 (CH$_2$-1), 36.6 (CH$_2$-12), 36.6 (CH$_2$-4), 37.5 (C-10), 42.8 (C-13), 47.9 (CH-14), 49.8 (CH-9), 73.1 (CH-3), 75.4 (CH-7), 82.2 (CH-17), 122.1 (CH-6), 144.2 (C-5), 170.3 (CH$_3$CO$_2$-3), 170.9 (CH$_3$CO$_2$-7), 171.0 (CH$_3$CO$_2$-17).

Bioconversion of (53) By *C. echinulata* var. *elegans*

Bioconversion of 53 using *C. echinulata* was generally carried out as for the other fungal species described supra. In these experiments, the steroid (53) (1 g), was dissolved in ethanol (20 mL) and added to a growing culture of the fungus as described above. The incubation period continued for five days after the last feed. Extraction of the broth and mycelia afforded an off-white solid (1.5 g) which was purified using column chromatography. Elution with 25% acetone in dichloromethane afforded unreacted steroid (232 mg). Continued elution afforded compound 56 (60 mg) which was identified by comparison of its spectral data with that of an authentic sample.

Continued elution afforded 3β,7β,17β-trihydroxyandrost-5-ene (54) (20.6 mg) which was identified by comparison of its spectral data with that of an authentic sample.

Immobilized Cell Fermentations

Media

Several types of culture media were tested in the fermentations using immobilized cells; potato broth, potato dextrose broth, and glucose solution. They were prepared as described below.

Potato Broth (PB)

Potato broth was made by dicing potatoes (300 g) and then boiling them in water (500 mL) until cooked. The resulting mixture was filtered through cloth. Water was then added to make the volume of the filtrate up to 1 L.

Potato Dextrose Broth (PDB)

Potato dextrose broth was made by dicing potatoes (300 g) and boiling them in water (500 mL) until cooked. The resulting mixture was filtered through cloth. Glucose (20 g) was added to the filtrate and the volume was made up to 1 L with water.

Glucose Solution

Glucose solution was prepared by dissolving glucose (10 g) in water (1 L).

Fermentation Conditions

In general, testing of biocatalysis using immobilized filamentous fungi was carried out as follows. Alginate beads containing filamentous fungi (fungal beads) were prepared as described herein. The beads (120 g) and sterilized PDB (500 mL) were added to four 500 mL erlenmeyer flasks. Steroid 53 (200 mg) in ethanol (5 mL) was added to the flasks. The immobilized cells and substrate were shaken at 180 rpm for five days, after which the aqueous medium was decanted from the alginate beads. The medium was extracted with ethyl acetate, dried with sodium sulfate, and the solvent was removed in vacuo. The resulting solid was purified using column chromatography.

Incubation of 53 with Immobilized Mycelia of *M. plumbeus*

To test immobilized *M. plumbeus* for biocatalysis products, steroid 53 (200 mg) was incubated with the alginate beads prepared from *M. plumbeus*. After five days of incubation, the fermentation was then worked up as described supra. The resulting solid (188 mg) was subjected to column chromatography. Elution with 25% acetone in dichloromethane afforded unreacted steroid (100 mg). Further elution resulted in 3β,7β,17β-trihydroxyandrost-5-ene (54) (84 mg), which was identified by comparison of its spectral data with that of an authentic sample.

Incubation of 53 with Immobilized Cells of *A. niger*

Immobilized *A. niger* were tested for biocatalysis using steroid 53 (200 mg). The compound was incubated with the alginate beads prepared from *A. niger*. The fermentation was then worked up after five days of incubation. The resulting solid (157 mg) was subjected to column chromatography. Elution with 25% acetone in dichloromethane afforded unreacted steroid (90 mg). Further elution yielded 3β,7β,17β-trihydroxyandrost-5-ene (54) (3 mg), which was identified by comparison of its spectral data with that of an authentic sample.

Incubation of 53 with Immobilized Cells of *R. oryzae*

Immobilized *R. oryzae* were tested for biocatalysis using steroid 53. The compound (200 mg) was incubated with the alginate beads prepared from *R. oryzae*. The fermentation was then worked up after five days of incubation. The resulting solid (172 mg) was subjected to column chromatography. Elution with 25% acetone in dichloromethane afforded unreacted steroid (80 mg). Further elution yielded 3β,7α,17β-trihydroxyandrost-5-ene (55) (10 mg), which was identified by comparison of its spectral data with that of an authentic sample.

Incubation of 53 with Immobilized Mycelia of *C. echinulata* Var. *elegans*

Steroid 53 (200 mg) was incubated with the alginate beads prepared from *C. echinulata* var. *elegans*. The fermentation was then worked up after 5 days. The resulting solid (168 mg) was subjected to column chromatography. Elution with 25% acetone in dichloromethane afforded unreacted steroid (110 mg). Further elution yielded 3β,17β-dihydroxyandrost-5-en-7-one (56) (5 mg) characterized as the diacetate (56a), gum, $[\alpha]_D$+58.8° (c=5.1, CHCl$_3$);

IR: $\nu_{max}$ 1736, 1217 cm$^{-1}$;

$^1$H NMR: δ 1.11 (3H, s, H-18), 1.37 (3H, s, H-19), 2.05 (3H, s, CH$_3$CO$_2$), 2.06 (3H, s, CH$_3$CO$_2$), 4.35 (1H, bs, H-17α), 4.63 (1H, t, J=5.1 Hz, H-3α), 6.10 (1H, s, H-6);

$^{13}$C NMR: δ 14.5 (CH$_3$-18), 19.6 (CH$_3$-19), 21.1 (CH$_3$ CO$_2$-3), 21.2 (CH$_3$CO$_2$-17), 22.0 (CH$_2$-15), 23.0 (CH$_2$-11), 27.3 (CH$_2$-2), 29.7 (CH$_2$-16), 32.7 (CH$_2$-1), 33.9 (CH$_2$-12), 36.0 (C-10), 42.4 (C-13), 43.7 (CH-8), 46.1 (CH$_2$-4), 46.9 (CH-9), 52.7 (CH-14), 67.5 (CH-3), 82.5 (CH-17), 130.0 (CH-6), 162.8 (C-5), 171.1 (CH$_3$CO$_2$-3), 172.0 (CH$_3$CO$_2$-17), 198.4 (C-7).

Continued elution produced 3β,7β,17β-trihydroxyandrost-5-ene (54) (5 mg), which was identified by comparison of its spectral data with that of an authentic sample.

Analysis of Results of Biotransformation of Steroids by Free Cells of *Mucor plumbeus* ATCC 4740

Free cells of *Mucor plumbeus* have been used to transform a number of steroids. Previously, it was reported that incubation with a 3-keto-$\Delta^{4,9(10)}$-19-norsteroid (1) resulted in the formation of the 11β-hydroxy compound (2) (Lacroix et al., *Bioorg. Med. Chem.*, 1999, 7, 2329-2341). 3β-Hydroxyandrost-5-en-17-one (3) and 17β-hydroxyandrost-4-en-3-one (6) were hydroxylated to afford compounds 4-5, and 7-9. Pregnenolone (10) also underwent 7β and 11α-hydroxylation to yield 11. However, the 3-ketosteroid, progesterone (12) was transformed exclusively to the 11α,14-dihydroxy derivative (13). The presence of the carbonyl group at C-20 seems crucial in the activity of the 11-hydroxylase enzyme. An estrane, estrone (14), was also transformed by the fungus to yield 15.

Analysis of Results of Bioconversion of Steroids by *Aspergillus niger* ATCC 9142

Progesterone (12) incubated with *A. niger* has been reported to result in production of the 21-hydroxy analog (16) (Holland et al., *Can. J. Chem.*, 1975, 53, 845-854). The presence of the C-20 carbonyl group has been found to be necessary for hydroxylation reactions to occur. In the absence of a carbonyl group at C-20 as in compounds 17 and 18 no oxygen insertion was observed. Instead the 11α-(19, 21) and 15β-hydroxylated (20, 22) congeners were formed (Holland, *Can. J. Chem.*, 1982, 53, 160-164). Dehydroepiandrosterone (3) has been converted to four products where oxidation of the C-3 hydroxyl group and migration of the C5-C6 double bond occurred (Yamashita et al., *Agric. Biol. Chem.*, 1976, 40, 505-509. CA 85:61352). Incubation with androst-4-ene-3,17-dione (27) resulted in the formation of the 18-hydroxy compound (28) (in 49% yield) and the 6p-hydroxy derivative (29) (Auret, *J. Chem. Soc. Chem. Comm.*, 1971, 1157).

In the present experiments, 7α and 16β-hydroxylation were observed, as well as C-3 oxidation accompanied by migration of the C-5,6 double bond to C-4,5 with 3β,17β-dihydroxyandrost-5-ene. With testosterone 6β and 16β-hydroxylation occurred.

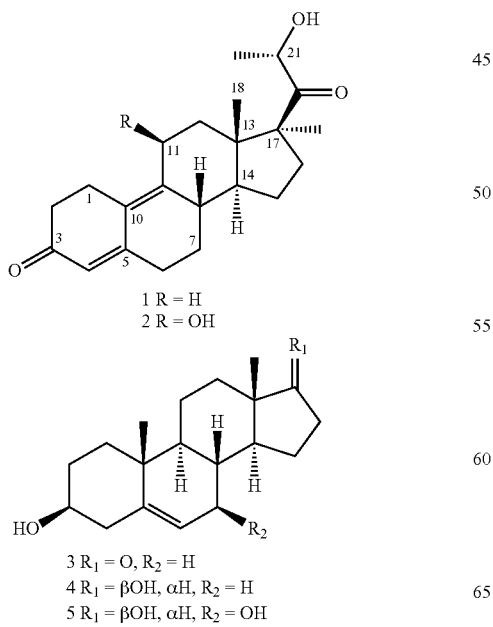

1 R = H
2 R = OH

3 R₁ = O, R₂ = H
4 R₁ = βOH, αH, R₂ = H
5 R₁ = βOH, αH, R₂ = OH

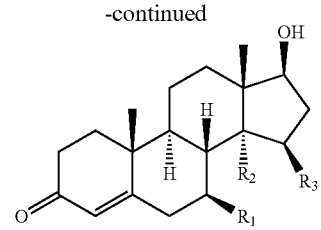

6 R₁ = R₂ = R₃ = H
7 R₁ = OH, R₂ = R₃ = H
8 R₁ = R₃ = H, R₂ = OH
9 R₁ = R₂ = H, R₃ = OH

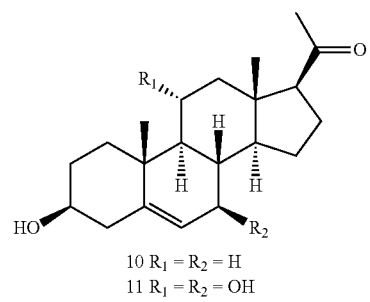

10 R₁ = R₂ = H
11 R₁ = R₂ = OH

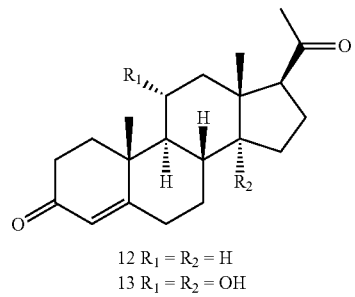

12 R₁ = R₂ = H
13 R₁ = R₂ = OH

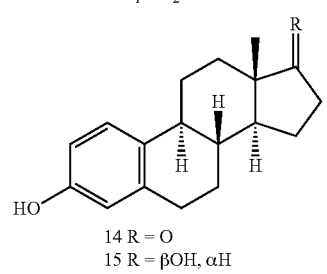

14 R = O
15 R = βOH, αH

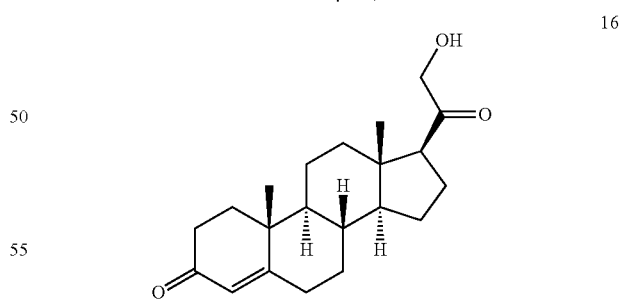

Analysis of Biotransformation of Steroids by *Rhizopus oryzae* ATCC 11145

Steroid transformations by *Rhizopus oryzae* (formerly known as *Rhizopus arrhizus*) ATCC 11145 have been documented. This biocatalyst has been incubated with a number of androstanes and pregnanes. The activity of both a 6β- and an 11α-hydroxylase was seen in compounds of the androstane series (Eppstein et al., *J. Chem. Soc.*, 1954, 76, 3174-

3179). Incubation of the $\Delta^4$-3-ketosteroids: 4-androstene-3,17-dione (27) and testosterone (6) yielded analogs 28-31 and 32-34 respectively.

The mechanism of this 6β-hydroxylase has been elucidated. The hydroxylation was thought to proceed via a $\Delta^{3,5}$-enol intermediate. In these experiments, the conversion of a $\Delta^{3,5}$-enol acetate (35) to various derivatives inclusive of the 6β-hydroxy-$\Delta^4$-3-keto compound confirmed the proposed mechanism (Holland et al., *Tetrahedron Lett.*, 1975, 44, 3787-3788).

When progesterone (12) was incubated with the fungus, the compound also underwent oxygen insertion at C-6 and 11 to give 36 and 37 (Peterson et al., *J. Am. Chem. Soc.*, 1952, 74, 5933-5936). *R. arrhizus* has also been used to effect side chain degradation. Crustecdysone (38), an insect molting hormone, was transformed to two products, a C-21 (39) and a C-17 (40) compound in fungal systems (Canonica et al., *J. Chem. Soc. Chem. Comm.*, 1974, 656-657).

In the present experiments using 3β,17β-dihydroxyandrost-5-ene; 7α and 7β-hydroxylations were observed. In the present experiments using testosterone; 1β,6β,7α, 11α-hydroxylations were observed.

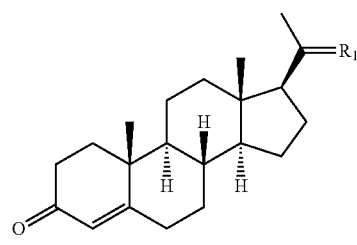

17 $R_1$ = βOH, αH
18 $R_1$ = αOH, βH

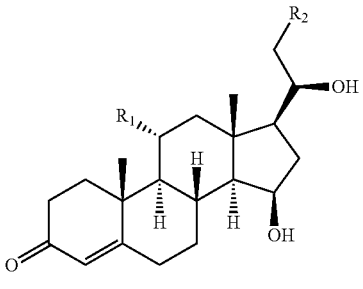

19 $R_1$ = $R_2$ = H
20 $R_1$ = OH, $R_2$ = H

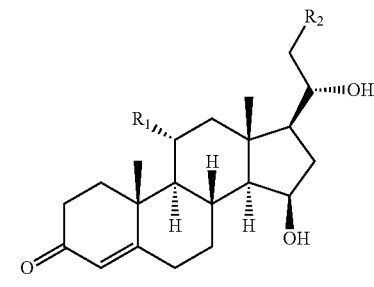

21 $R_1$ = $R_2$ = H
22 $R_1$ = OH, $R_2$ = H

-continued

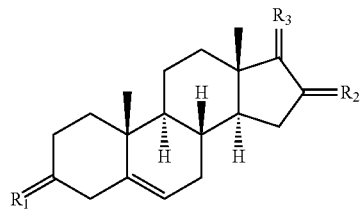

3 $R_1$ = βOH, αH, $R_2$ = $H_2$, $R_3$ = O
23 $R_1$ = $R_3$ = O, $R_2$ = $H_2$
24 $R_1$ = $R_2$ = O, $R_3$ = βOH, αH
25 $R_1$ = O, $R_2$ = $R_3$ = βOH, αH
26 $R_1$ = $R_3$ = O, $R_2$ = βOH, αH

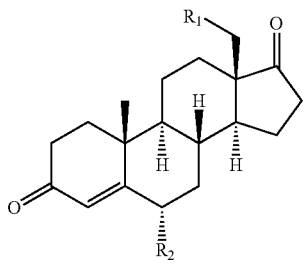

27 $R_1$ = $R_2$ = H
28 $R_1$ = OH, $R_2$ = H
29 $R_1$ = H, $R_2$ = OH

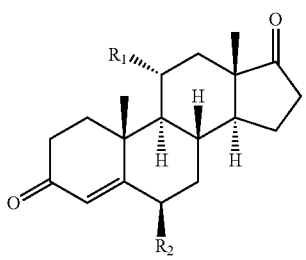

30 $R_1$ = H, $R_2$ = OH
31 $R_1$ = OH, $R_2$ = H

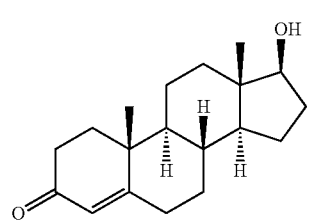

6

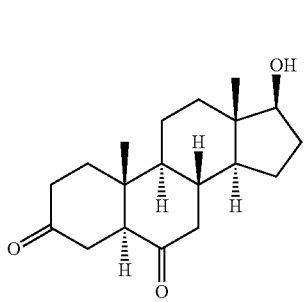

32

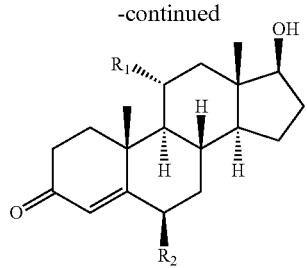

33 R₁ = H, R₂ = OH
34 R₁ = OH, R₂ = H

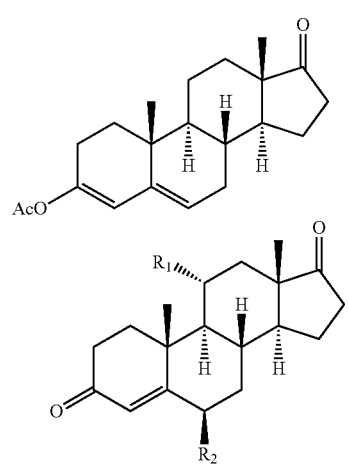

27 R₁ = R₂ = H
30 R₁ = H, R₂ = OH
31 R₁ = OH, R₂ = H

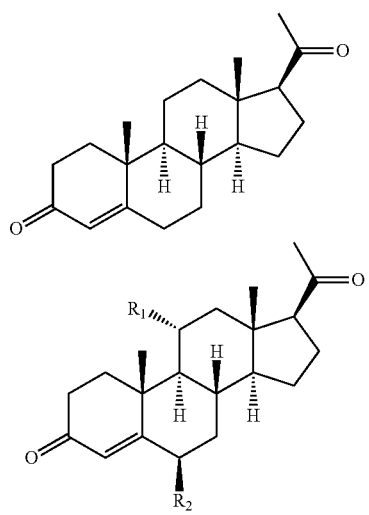

36 R₁ = H, R₂ = OH
37 R₁ = OH, R₂ = H

Biotransformation of Steroids by *Cunninghamella echinulata* Var. *elegans* ATCC 8688A The potential of *Cunninghamella echinulata* var. *elegans* ATCC 8688a (formerly known as *C. blakesleeana*) as a biological agent for the conversion of steroids has been investigated (Hu et al., *Steroids*, 1988, 63, 88-92; Garcia-Rodriguez et al., *Khim. Farm. Zh.*, 1981, 15, 73-75. CA 96:65383; Kaneko et al., *Chem. Pharm. Bull. Jpn.*, 1969, 17, 2031-2035. CA 72:29055). Incubation of the deoxycorticos- terone, 6α-methyl-11-deoxy-17α-hydroxycorticosterone (41), with the fungus yielded two analogs, 42 and 43. Cortexolone (44) underwent hydroxylation at the C-11 position (Garcia-Rodriguez et al., *Khim. Farm. Zh.*, 1978, 12, 95-97. CA 90:20769). Diosgenin (48), a synthon used in the preparation of other steroids, was hydroxylated at C-7, 11 and 12 (Kaneko, *Chem. Pharm. Bull. Jpn.*, 1969, 17, 2031-2035. CA 72:29055).

In the present experiments using 3β,17β-dihydroxyandrost-5-ene; 7α and 7β-hydroxylations were observed and in experiments using testosterone; 6β,7α,14α-hydroxylations were observed.

Bioconversion of 3β,17β-DIHYDROXYANDROST-5-ENE (53)

When the commercially available 3β-androst-5-en-17-one (52) was incubated with *M. plumbeus*, the keto group was first reduced to yield 3β,17β-dihydroxyandrost-5-ene (53), which was then hydroxylated. It was thought that feeding 53 rather than 52 would simplify analysis of the metabolites. Steroid 52 was therefore chemically reduced to the known 3β,17β diol (53) (Pearson et al., *J. Chem. Soc. Perkin Trans.* 1, 1985, 267) which was incubated with the free and immobilized cells. The products obtained from each incubation were then compared.

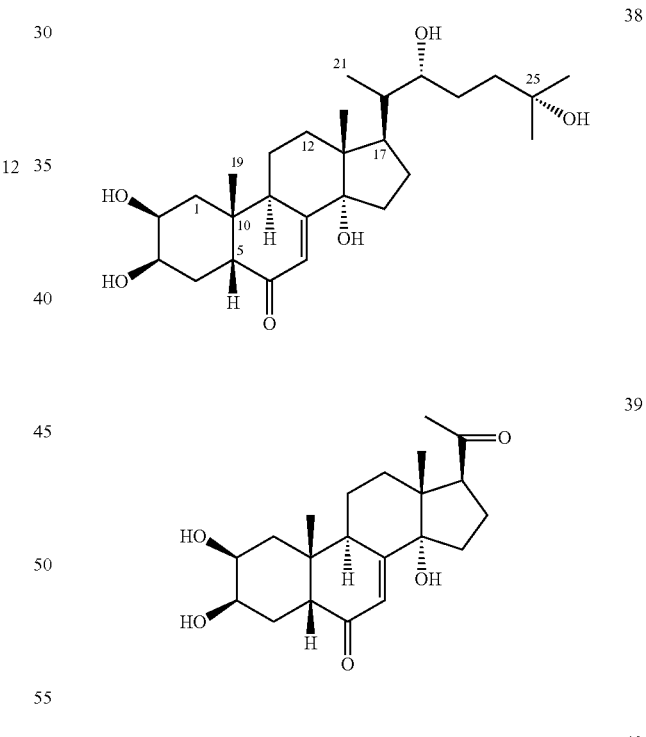

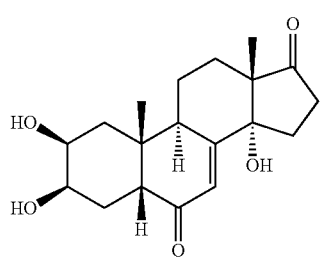

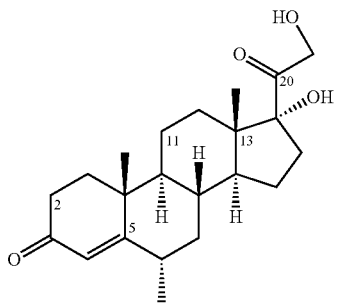

41

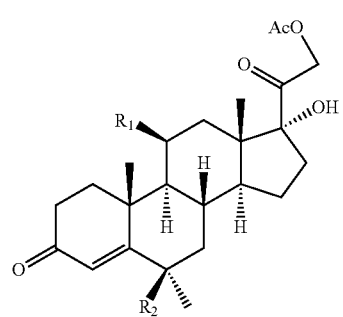

42 R₁ = R₂ = OH
43 R₁ = H, R₂ = OH

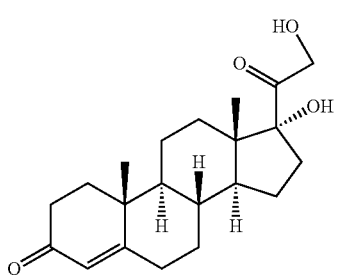

44

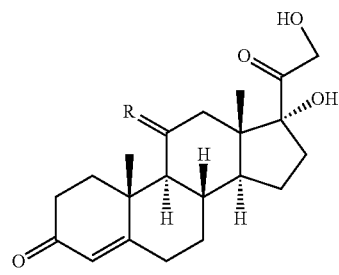

45 R = αOH, βH
46 R = βOH, αH
47 R = O

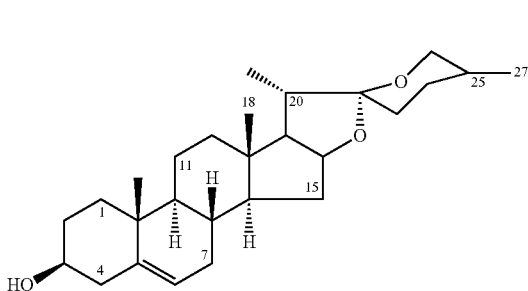

48

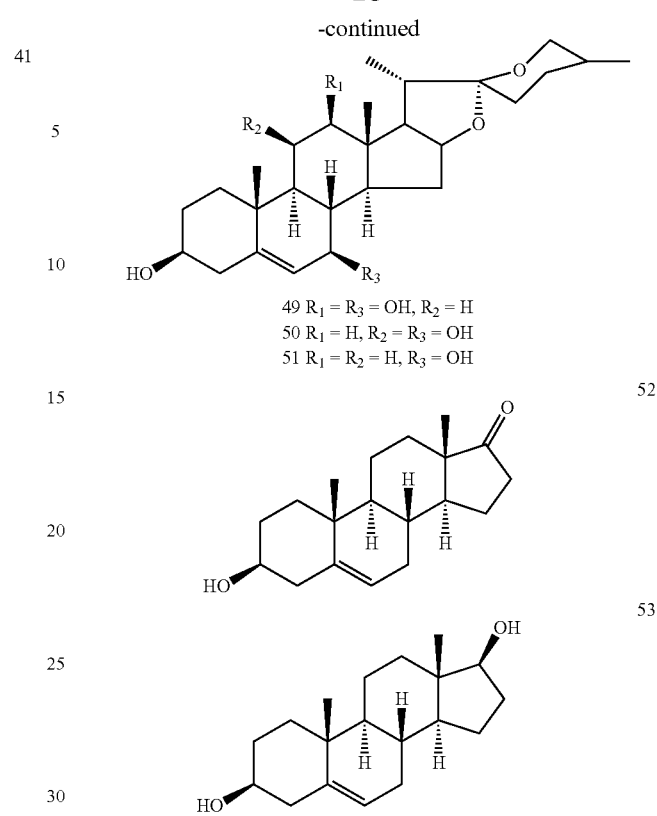

49 R₁ = R₃ = OH, R₂ = H
50 R₁ = H, R₂ = R₃ = OH
51 R₁ = R₂ = H, R₃ = OH

52

53

Example 2

Additional Experiments Using Free Fungal Cells

Experiments were repeated as described above and an additional analysis of products was performed. The results are as follows.

Incubation of 3β,17β-DIHYDROXYANDROST-5-ENE (53) with *Mucor plumbeus* ATCC 4740

Analog 54, obtained in 61% yield, was acetylated for characterization purposes. A signal at δ 4.96 in the ¹H NMR spectrum of congener 54a was observed. Examination of the ¹³C and DEPT NMR spectra showed a new methine at δ 67.5. This was coupled with the loss of methylene at δ 31.3 (C-7). Shifts in neighboring carbon resonance values indicated that hydroxylation had occurred at C-7 to yield the 3β,7β,17β-trihydroxyandrost-5-ene (54).

Incubation of 3β,17β-DIHYDROXYANDROST-5-ENE (53) with *Aspergillus niger* ATCC 9142

Compound 54 was also isolated from *A. niger*. However, the compound was obtained in a much lower yield (6.6%) compared to the yield from *M. plumbeus*.

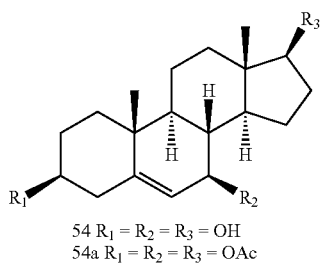

54 R₁ = R₂ = R₃ = OH
54a R₁ = R₂ = R₃ = OAc

Bioconversion of 3β,17β-DIHYDROXYANDROST-5-ENE (53) by *Rhizopus oryzae* ATCC 11145

Compound 55, the sole product of the biotransformation using *R. oryzae*, was characterized as the triacetate. The molecular formula obtained ($C_{25}H_{36}O_6$) from $^{13}C$ and DEPT NMR data for 55a was the same as that for 54a. However, the $^{13}C$ NMR spectrum was slightly different compared to 54a. A new methine at δ 74.5 was seen in the $^{13}C$ NMR spectrum, and this was accompanied by the loss of the C-7 methylene at δ 31.3. It was therefore concluded that 55 was the known compound, 3β,7α,17β-trihydroxyandrost-5-ene (Wilson et al., *Steroids,* 1999, 64, 834-843).

Incubation of 3β,17β-DIHYDROXYANDROST-5-ENE (53) with *Cunninghamella echinulata* Var. *elegans* ATCC 8688A Analog 56, which was produced after incubation of *C. echinulata* with 53, was found to possess a new nonprotonated carbon at δ 198.4. There was a noticeable downfield shift of 11.1 ppm for C-8. Further examination of the $^{13}C$ NMR spectrum showed the loss of the C-7 methylene at 31.4 ppm. Therefore, 56 was determined to be 3β,17β-dihydroxyandrost-5-en-7-one. The second metabolite isolated from this incubation was 54.

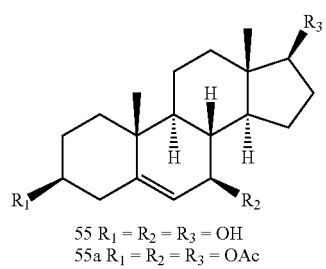

55 $R_1 = R_2 = R_3 = OH$
55a $R_1 = R_2 = R_3 = OAc$

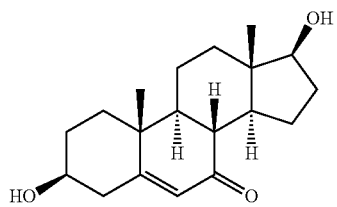

56

Biotransformations Using Immobilized Cells

To further investigate biotransformations using immobilized mycelia, mycelia of *M. plumbeus, A. niger, R. oryzae* and *C. echinulata* var. *elegans* were immobilized in a calcium alginate matrix as described supra. Alginic acid is the major polysaccharide of several genera of marine brown algae. Alginate beads (containing trapped viable mycelia) were formed by dripping a suspension of the fungal cells in aqueous sodium alginate into a stirred solution of calcium chloride as described herein. Gelation occurred as a result of displacement of the monovalent sodium ion by the divalent calcium ion. This caused cross-linking of the polysaccharide. Alginate beads produced from the four fungi were suspended in solutions of distilled water and solutions of 53 in ethanol were incubated with each. The incubations were carried out for five days, after which the aqueous solutions were decanted from the beads and then were extracted with ethyl acetate.

Incubation of 3β,17β-DIHYDROXYANDROST-5-ENE (53) with *M. plumbeus*

Incubation of 53 with *M. plumbeus* resulted in formation of a single more polar metabolite, which was identified as 54. This same metabolite was also isolated from the free cell fermentations. This demonstrates an example in which the immobilization of a filamentous fungus for use in a biotransformation results in the production of the same compound as is produced by the free fungus.

Biotransformation of 3β,17β-DIHYDROXYANDROST-5-ENE (53) by *A. niger*

Incubation of 53 with *A. niger* also resulted in production of the metabolite 54. This is the same result as when free *A. niger* was fermented with 53.

Incubation of 3β,17β-DIHYDROXYANDROST-5-ENE (53) with *R. oryzae*

Two metabolites, more polar than 53, were isolated from the extract of this incubation. They were found to be compounds 54 and 55.

Incubation of 3β,17β-DIHYDROXYANDROST-5-ENE (53) with *C. Echinulata* var. *elegans*

The incubation of 53 with immobilized *C. echinulata* resulted in the isolation of analogs 54 and 56.

While the products obtained from the immobilized cell fermentations were the same as those from the free cell fermentations the yields from the former were lower. The alginate beads were then tested for viability. Two week old "spent" alginate beads that had been stored at 4° C. were re-incubated with compound 53. At the end of the incubation period the physical integrity of the alginate beads had not been compromised. Although hydroxylation of the xenobiote was observed it was obvious that some loss of enzymatic activity had occurred since the previous incubation. Despite the lower yields, the results demonstrate that the alginate beads containing mycelia have the potential for reuse.

Example 3

Optimization of Yields in Fermentations Using Immobilized Fungi

Homogenization (Maceration) Time

To increase the yields from the incubations various parameters were modified. It was thought that the size of the cell fragments affected the stability of the alginate beads as the larger fragments would result in fissures of the alginate beads. Therefore, mycelia were macerated to create smaller fragments. Maceration of mycelia to be immobilized has not been previously reported. Fungal hyphae are divided into compartments, similar to cells, by septa. Hyphae with large compartments will therefore lose enzymatic activity because fewer and fewer cells remain as maceration continued. It was observed that mycelium that was macerated for longer than 3 minutes retained little or no enzymatic activity. Based on the results the mycelia were macerated for 3 minutes at 8,000 rev/min.

This demonstrates that maceration can be performed and the resulting cells, once immobilized, are still viable. It also demonstrates a method for determining the amount of maceration that is useful, i.e., that does not destroy the enzymatic activity of the cells.

TABLE 1

Effect of time of homogenization on
transformation yields (%) of different fungi

| | Homogenization time at 8000 rev/min | | | |
|---|---|---|---|---|
| | 1 min. | 3 min. | 5 min. | 7 min. |
| M. plumbeus (% transformation) | 10 | 31 | 8 | 2 |
| A. niger (% transformation) | 4 | 7 | 1 | 1 |
| R. oryzae (% transformation) | 9 | 12 | 8 | 1 |

Bead Diameter

In any fermentation procedure the rate at which a compound added to the culture medium (xenobiotes) diffuses into the mycelia is important because this rate can affect the yield of transformation. This is also true of incubations involving immobilized cells. The compounds have to diffuse through not one, but two, semipermeable barriers (gel matrix and cell membrane). The surface area:volume ratio is a function of the diameter of the alginate beads. Therefore, the bead diameter influences the outcome of biocatalysis incubations using fungal beads. Therefore, experiments were conducted to identify a bead size that would produce relatively high transformation yields. Different bead sizes were achieved by varying the diameter of the bore of the dropping tube, and were tested using several different fungal species.

The results of these experiments are provided in Table 2 and indicate that the optimal bead diameter was 3 mm. Transformation yields were reduced with the larger alginate beads.

TABLE 2

Effect of varying bead diameter on
transformation yields (%) of different fungi

| | Alginate bead diameter/mm | | |
|---|---|---|---|
| | 1 mm | 3 mm | 5 mm |
| M. plumbeus (% transformation) | 10% | 31% | 7% |
| A. niger (% transformation) | 3% | 5% | 1% |
| R. oryzae (% transformation) | 6% | 12% | 8% |

Media for Rejuvenation of Fungal Beads

Some enzymes require cofactors to carry out their reactions. Exhausted cofactors have to be replenished before further reactions will take place. Replenishment of stores of the cofactor NADPH is crucial for the success of cytochrome P450 hydroxylations. Four possible media were investigated: water, 1% glucose solution, potato broth (PB) and potato dextrose broth (PDB). In these experiments, immobilized cells that had been used in a biocatalysis reaction (termed "exhausted" immobilized cells) were incubated in one of the four media with shaking for 12 hours. The beads were then washed with water and were reincubated with the steroid. Incubation in PDB produced the best results overall. Cells that were incubated in the glucose solution exhibited growth of the mycelia out of the bead framework, which led to the collapse of the matrix. It was concluded that the enzymes in the cells needed nutrients and inorganic salts for regeneration of the cofactors. PDB was generally a good medium for rejuvenation of the beads after use (Table 3), although other media were effective. A more dilute glucose solution may be useful, i.e., a solution that does not support vigorous growth of mycelia in fungal beads.

These data demonstrate that immobilized cells in alginate beads can be reused, and that incubation in a suitable medium increases yields of biocatalysis products.

TABLE 3

Effect of different types of media (for rejuvenation)
on biocatalysis yields (%) of 53 using various fungi

| | Rejuvenation Medium | | | |
|---|---|---|---|---|
| | $H_2O$ | Glucose | PB | PDB |
| M. plumbeus (% transformation) | 19 | 23 | 20 | 49 |
| A. niger (% transformation) | 1 | 3 | 1 | 5 |
| R. oryzae (% transformation) | 3 | 7 | 7 | 11 |

Storage of Fungal Beads

Conditions for storage of fungal beads were tested. In this experiment, fungal beds that were prepared as described herein were stored in distilled water or PDB, then were used for biotransformation of 53. The percentage of metabolites resulting from the biotransformation was then assayed. It was found that in general, storage of the beads in water or PDB prior to their first use were equally effective and had very little effect on the transformation yield. M. plumbeus was an exception (Table 4) for which storage in PDB resulted in higher biotransformation yields.

TABLE 4

Effect of storing the beads in water or PDB, prior to
transformation, on yields (%) of metabolites of 53

| Fungi | Water | Potato Dextrose Broth (PDB) |
|---|---|---|
| R. oryzae (% transformation) | 49.7 | 50 |
| M. plumbeus (% transformation) | 42.9 | 70.6 |
| A. niger (% transformation) | 27.2 | 23.6 |
| C. echinulata var. elegans (% transformation) | 63.2 | 56.7 |

Example 4

Additional Experiments Demonstrating the Use of Fungal Beads

Six species of filamentous fungi were selected for additional testing in the new method using fungal beads, specifically *Rhizopus oryzae* (ATCC 11145), *Mucor plumbeus* (ATCC 4740), *Cunninghamella echinulata* var. *elegans* (ATCC 8688a), *Aspergillus niger* (ATCC 9142), *Phanerochaete chrysosporium* (ATCC 24725) and *Whetzelinia sclerotiorum* (ATCC 18687).

Both 3β,17β-dihydroxyandrost-5-ene (53) and 17β-hydroxyandrost-4-en-3-one (testosterone) (2) served as substrates in these additional studies.

In general, immobilized cells were prepared as described above. Initial cultures of fungi were prepared as follows.

*Mucor plumbeus* was maintained on potato dextrose agar slants at 28° C. Five slants were used to inoculate twenty 500 mL Erlenmeyer flasks each containing 125 mL liquid culture medium. The medium was prepared using glucose (30 g/L), potassium chloride (0.5 g/L), corn steep solids (5 g/L), sodium nitrate (2 g/L), magnesium sulfate heptahydrate (0.5 g/L), and iron(II) sulfate (0.02 g/L). The flasks were shaken at 250 rpm.

*Rhizopus oryzae* was maintained on malt agar slants at 28° C. Five slants were used to inoculate twenty 500 mL Erlenmeyer flask each containing 125 mL liquid culture. The medium was prepared from glucose (20 g/L), peptone (5 g/L), sodium chloride (5 g/L) and yeast extract (5 g/L). The flasks were shaken at 250 rpm.

*Aspergillus niger* was maintained on potato dextrose agar slants at 28° C. Five slants were used to inoculate twenty 500 mL Erlenmeyer flasks each containing 125 mL of liquid culture. The medium was prepared using glucose (20 g/L), yeast extract (5 g/L), soya meal (5 g/L) sodium chloride (5 g/L) and dipotassium hydrogen phosphate (5 g/L). The flasks were shaken at 180 rpm.

*Cunninghamella echinulata* var. *elegans* was maintained on maltose-peptone slants at 28° C. Five slants were used to inoculate twenty 500 mL Erlenmeyer flasks each containing 125 mL of liquid culture. The medium was prepared using glucose (20 g/L), yeast extract (5 g/L), soya meal (5 g/L), sodium chloride (5 g/L) and dipotassium hydrogen phosphate (5 g/L). The flasks were shaken at 180 rpm.

*Whetzelinia sclerotiorum* was maintained on potato dextrose agar slants at 28°. Five slants were used to inoculate twenty 500 mL Erlenmeyer flasks each containing 125 mL of liquid culture. The medium was made using potassium nitrate (10 g/L), magnesium sulfate heptahydrate (1.5 g/L), potassium dihydrogen phosphate (2.5 g/L), glucose (0.5 g/L), yeast extract (0.5 g/L) and cellulose (10 g/L). The flasks were shaken at 180 rpm.

*Phanerochaete chrysosporium* was maintained on potato dextrose agar slants at 28° C. Five slants were used to inoculate twenty 500 mL Erlenmeyer flasks each containing 125 mL of liquid culture. The medium was made using potassium nitrate (10 g/L), magnesium sulfate heptahydrate (1.5 g/L), potassium dihydrogen phosphate (2.5 g/L), glucose (40 g/L), and yeast extract (2 g/L). The flasks were shaken at 180 rpm.

Preparation of Immobilized Fungal Cells

In general, cells from filamentous fungi were prepared for incorporation into beads as described supra. One slant was used to inoculate four Erlenmeyer flasks each containing 125 mL liquid culture medium. The fungus was allowed to grow for 3 days with shaking, cells were harvested by filtration, suspended in water (10 mL) and then were macerated in a 3% sodium alginate solution (35 mL). The cell-alginate suspension was then added drop wise to a stirred chilled solution of 0.1 M calcium chloride (200 mL). Once formed, the alginate beads were allowed to harden for 30 minutes in the calcium chloride solution. The calcium chloride was decanted and the beads were rinsed with water. The beads were stored in water at 4° C.

Immobilized Cell Fermentation Conditions

For fermentations using fungal beads in these experiments, alginate beads were divided into for equal portions (about 50 mL) and placed into four 500 mL Erlenmeyer flasks each containing water (125 mL). The substrate compound (200 mg) in ethanol (5 mL) was added to the flasks. The flasks were shaken at 180 rpm for five days.

After the fermentation was complete the water was decanted from the beads and the former was extracted using ethyl acetate (2×300 mL). The organic solution was dried using sodium sulfate, filtered, and the solvent was removed in vacuo. The residue was analyzed by TLC and purified by column chromatography. The characterization of some metabolites was aided by their acetylation and further purifications, thereby permitting identification of products, some of which were not identified in the initial experiments.

Results with 3β,17β-DIHYDROXYANDROST-5-ENE (53) as Substrate *Rhizopus oryzae* ATCC 11145

Two analogs were isolated from the fermentation of free *R. oryzae* with 3β,17β-dihydroxyandrost-5-ene (53) as a substrate for biocatalysis; 3β,7α,17β-trihydroxyandrost-5-ene (55) and 3β,7α,17β-trihydroxyandrost-5-ene (54). Incubation of the immobilized cells (i.e., fungal beads) also produced compounds 55 and 54, as well as 3β,7β-dihydroxyandrost-5-en-17-one (59) was also produced by the cells in fungal beads.

These data demonstrate that in addition to producing the same products as free cells, in some cases, additional compounds are generated by immobilized cells.

*Mucor plumbeus* ATCC 4740

The incubation of both the free and immobilized cells of *M. plumbeus* resulted in production of two metabolites: 3β,7α,17β-trihydroxyandrost-5-ene (54) and 3β,7α-dihydroxyandrost-5-en-17-one (60).

These data demonstrate that in addition to producing the same products as free cells, in some cases, additional compounds are generated by immobilized cells.

*Cunninghamella echinulata* var. *elegans* ATCC 8688a

The fermentations of both free and immobilized *C. echinulata* cells produced two derivatives: 3α,7α,17β-trihydroxyandrost-5-ene (55) and 3β,7β,17β-trihydroxyandrost-5-ene (54).

*Aspergillus niger* ATCC 9142

The same three analogs were isolated from the free and immobilized cell incubations using *A. niger*; 3β,7α,17β-trihydroxyandrost-5-ene (55), 17β-hydroxyandrost-4-en-3-one (58) and 17β-hydroxyandrost-4-ene-3,16-dione (61).

*Phanerochaete chrysosporium* ATCC 24725

In experiments using *P. chrysosporium*, most of the substrate (53) remained unchanged in this fermentation for both free and immobilized cells. The metabolites that were formed included multiple products, the quantities of each were too small for characterization under the conditions available.

*Whetzelinia sclerotiorum* ATCC 18687

This fermentation of free cells of *W. sclerotorum* resulted in production of four compounds; 3β,7α,17β-trihydroxyandrost-5-ene (55), 3β,7β,17β-trihydroxyandrost-5-ene (54), 3β,7β-dihydroxyandrost-5-en-17-one (59) and 3β,5α,6β,17β-tetrahydroxyandrostane (62). Fermentation of immobilized cells resulted in production of compounds 58, 54, and 62. However, compound 59 was not isolated from the immobilized cells.

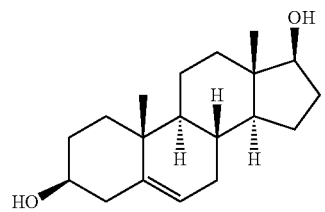

1

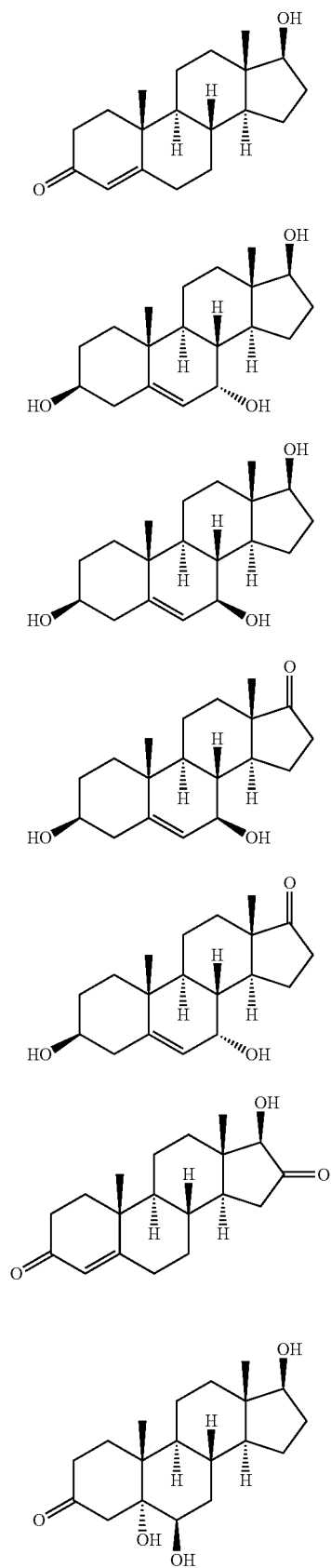

Fungal Bioconversions Using Testosterone (57) as Substrate
Rhizopus oryzae ATCC 11145

Six compounds were isolated from this fermentation of *R. oryzai* cells with testosterone; 6β,17β-dihydroxyandrost-4-en-3-one (63), 11α,17β-dihydroxyandrost-4-en-3-one (64), 6β-hydroxyandrost-4-ene-3,17-dione (65), 1β,17β-dihydroxyandrost-4-en-3-one (66), 7α,17β-dihydroxyandrost-4-en-3-one (67) and 6β,11α,17β-trihydroxyandrost-4-en-3-one (68). Fermentation using immobilized cells produced similar results except that compound 66 was not formed.

Mucor plumbeus ATCC 4740

The incubation of free cells of *M. plumbeus* resulted in eight metabolites; 6β,17β-dihydroxyandrost-4-en-3-one (63), 6β-hydroxyandrost-4-ene-3,17-dione (65), 7α,17β-dihydroxyandrost-4-en-3-one (67), 14α,17β-dihydroxyandrost-4-en-3-one (69), 6β,14α-dihydroxyandrost-4-ene-3,17-dione (70), 15α,17β-dihydroxyandrost-4-en-3-one (71), 6β,14α,17β-trihydroxyandrost-4-en-3-one (72) and 14α-hydroxyandrost-4-ene-3,17-dione (73). Fermentation of immobilized cells resulted in production of the same products except that compounds 70 and 72 were not detected.

Cunninghamella echinulata Var. elegans ATCC 8688A

Fermentation of free cells of *C. echinulata* resulted in production of three analogs; 6β,17β-dihydroxyandrost-4-en-3-one (63), 7α,17β-dihydroxyandrost-4-en-3-one (67), and 14α,17β-dihydroxyandrost-4-en-3-one (69). The immobilized cell fermentation produced compounds 67 and 69. However, compound 63 was not found. An additional compound was isolated; 14α-hydroxyandrost-4-ene-3,17-dione (73).

Aspergillus niger ATCC 9142

Five products of biotransformation were isolated from the free cell fermentation of *A. niger;* 6β,17β-dihydroxyandrost-4-en-3-one (63), 16β,17β-dihydroxyandrost-4-en-3-one (74), 16β-hydroxyandrost-4-ene-3,17-dione (75), 16β, 17α-dihydroxyandrost-4-en-3-one (76) and 17β-hydroxyandrost-4-ene-3,16-dione (61). The immobilized cell fermentation produced four metabolites, including compounds 63 and 74. However, compounds 75, 76, and 61 were not isolated. In addition, 11α,17β-dihydroxyandrost-4-en-3-one (64) and 17β-hydroxyandrosta-1,4-dien-3-one (77) were isolated from this incubation.

Phanerochaete chrysosporium ATCC 24725

The incubation of the free cells of *P. chrysosporium* resulted in the production of four analogs; 15β,17β-dihydroxyandrost-4-en-3-one (78), 6β-hydroxyandrost-4-ene-3,17-dione (70), androst-4-ene-3,17-dione (79), and 17β-hydroxy-5α-androstan-3-one (80). The immobilized cell fermentation also produced four steroid compounds. However, only two of these metabolites, compounds 70 and 78, had been formed in the free cell fermentation. The other two products produced by the immobilized cells were 6β,17β-dihydroxyandrost-4-en-3-one (63) and 11α,17β-dihydroxyandrost-4-en-3-one (64).

Whetzelinia sclerotiorum ATCC 18687

Eight metabolites were isolated from the free cell fermentation of *W. sclerotorum;* 2β,6β-dihydroxyandrost-4-ene-3,17-dione (81), 2β,17β-dihydroxyandrost-4-en-3-one (82), 2β,16β-dihydroxyandrost-4-ene-3,17-dione (83), 2β,15β,17β-trihydroxyandrost-4-en-3-one (84), 7α,17β-dihydroxyandrost-4-en-3-one (67), 2,6β-dihydroxyandrosta-1,4-diene-3,17-dione (85), 2,6β,17β-trihydroxyandrosta-1,4-dien-3-one (86), and 17β-hydroxyandrosta-1,4-dien-3-one (77). The immobilized cell incubation produced eight analogs, four of which were the same as those isolated from the free cell fermentation (compounds 81, 82, 83, and 84). The other four products were 2β,6β,17β-trihydroxyandrost-4-en-3-one (87), 6β,17β-dihydroxyandrost-4-en-3-one (63), 2β,11α,17β-trihydroxyandrost-4-en-3-one (88), and 2β,3α, 17β-trihydroxyandrost-4-ene (89).
9
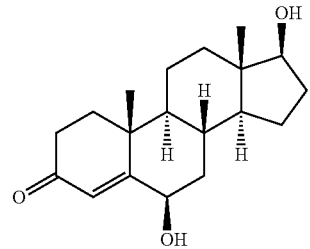
10
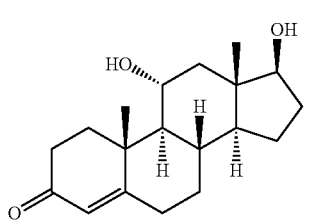
11
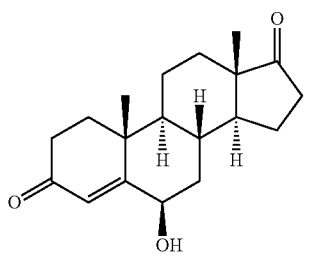
12
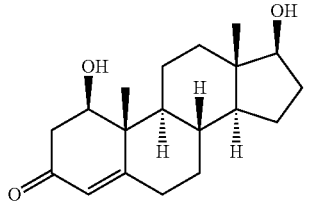
13
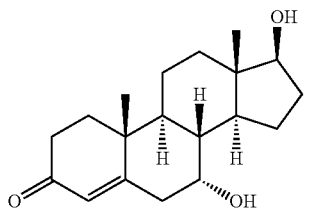
14
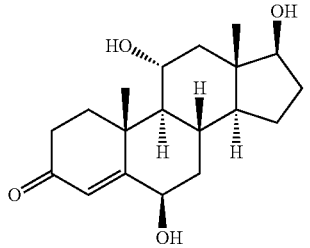
-continued
15
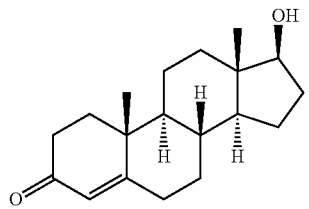
16
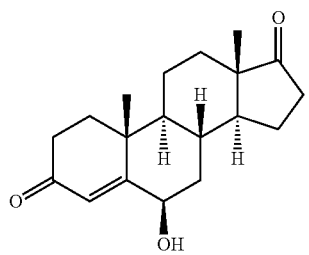
17
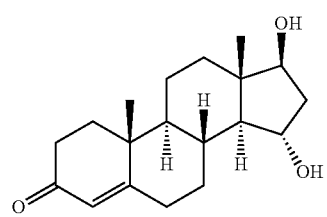
18
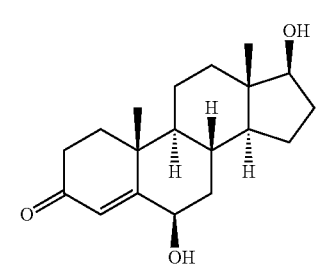
19
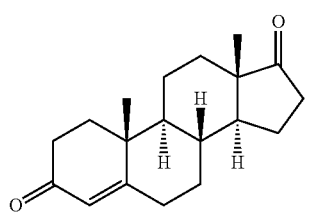
20
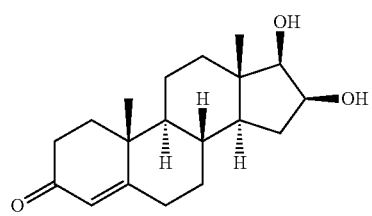
21
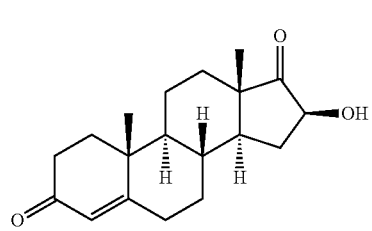

22
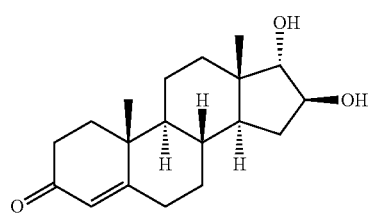
23
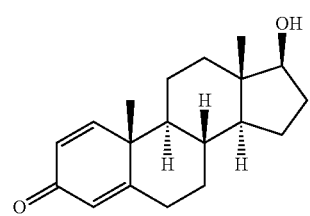
24
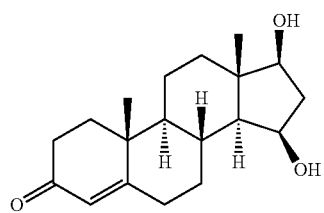
25
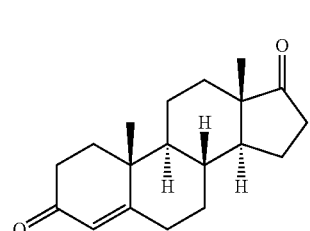
26
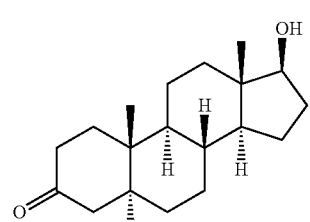
27
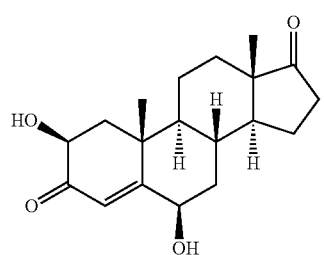
28
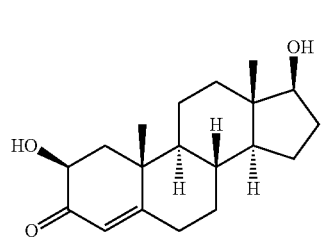
29
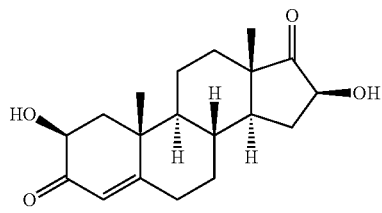
30
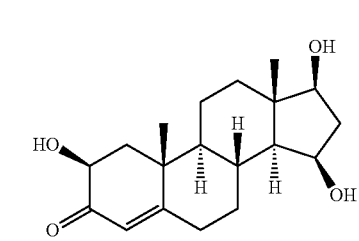
31
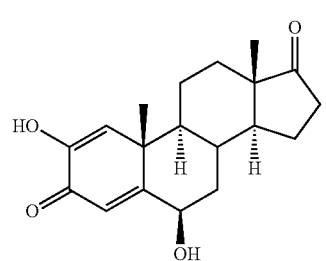
32
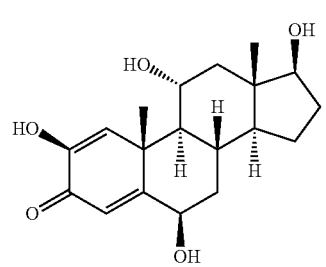
33
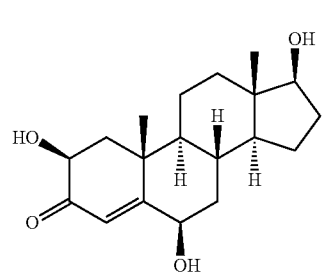
34
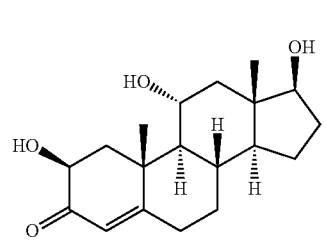

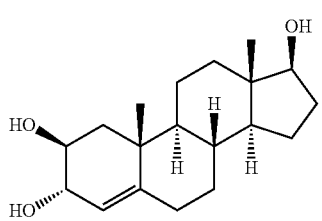

Example 5

Mixed Cell Biotransformations: Bioconversion Using Multiple Types of Fungal Beads The need for more polar analogs of steroids as potential pharmaceuticals is well known. One method of generating more functionalized steroid analogs is by incubation of the substrate first with one fungus, isolating the metabolites and feeding them to a second microorganism. An easier operation, in theory, would involve feeding a compound to a culture vessel containing two different fungi. However, because two different microorganisms are unlikely to grow at the same rate and may produce antimicrobial compounds affecting growth of the co-cultured fungi of different types, this approach is impractical. Immobilized cells provide a method for co-culturing two types of filamentous fungi to produce products. This approach avoids cell growth issues because the cells are already grown and do not produce detectable amounts of secondary metabolites. As described above, preliminary experiments indicated that fungal beads were useful for such biotransformations.

Having ascertained that the products of incubation from the free and entrapped cells were generally the same, the subsequent course of action was to investigate incubations using mixed alginate beads derived from two fungi. Such a system would offer the potential for transformed compounds of one fungus becoming substrates for the other. Therefore, so-called "crossover" products may be formed. This would result in the production of multiple products of transformation. This system therefore can carry out a type of combinatorial biotransformation. Initial experiments were carried out to determine whether additional compounds can be made using multiple types of fungal beads.

Bioconversion of 53 by Immobilized Cells of M. plumbeus and R. oryzae

Alginate beads derived from two different species of fungus (60 g) were distributed over four 500 mL flasks each containing 125 mL sterilized PDB. Steroid 53 (200 mg) in ethanol (5 mL) was added to the flasks. The immobilized cells and substrate were shaken at 180 rpm for five days. The aqueous medium was decanted, extracted with ethyl acetate, dried with sodium sulfate, and the solvent was removed in vacuo. The resulting solid (171.4 mg) was purified using column chromatography. Elution with 25% acetone in dichloromethane afforded the original steroid (53) (10 mg). Further elution yielded 3β,7β,11α,17β-tetrahydroxyandrost-5-ene (90) (5 mg) which resisted crystallization, $[\alpha]_D$+20.4° (c=3.1, CHCl$_3$);

IR: $\nu_{max}$ 3454, 1220 cm$^{-1}$;

HREIMS: m/z (rel. int.) 304.2039 (10) [M-H$_2$O]$^+$ (304.2144 calcd. for C$_{19}$H$_{30}$O$_4$—H$_2$O), 302.1882 (3), 288.2086 (4), 286.1933 (4) [M-2H$_2$O]$^+$;

$^1$H NMR: δ 0.78 (3H, s, H-18), 1.01 (3H, s, H-19), 3.54 (1H, m, W/2=7.3 Hz, H-17a), 3.47 (1H, m, W/2=7.0 Hz, H-11a), 4.02 (1H, m, W/2=7.0 Hz, H-7a), 5.31 (1H, d, J=4.7 Hz, H-6); $^{13}$C NMR: δ 14.1 (CH$_3$-18), 19.6 (CH$_3$-19), 27.7 (CH$_2$-15), 30.0 (CH$_2$-16), 32.8 (CH$_2$-2), 34.6 (CH-8), 36.5 (C-10), 36.8 (CH$_2$-1), 38.1 (CH$_2$-4), 46.1 (CH-9), 48.5 (CH-14), 50.1 (CH$_2$-12), 50.7 (C-13), 65.4 (CH-11), 70.0 (CH-7), 72.4 (CH-3), 81.9 (CH-17), 120.5 (CH-6), 139.4 (C-5).

The extract from the M. plumbeus/R. oryzae system contained the metabolites that were seen from the individual free cell incubations as well as a new compound. This metabolite (90) possessed a molecular formula of C$_{19}$H$_{30}$O$_4$ based on $^{13}$C and DEPT NMR data. Two new methines at δ 65.4 and 70.0 were observed. The absence of two methylenes at 20.4 (C-11) and 31.4 ppm (C-7) were also noted. It was then concluded that analog (90) was the 3β,7β,17β-tetrahydroxyandrost-5-ene.

Because compound (90) was not produced by M. plumbeus or R. oryzae when either was incubated alone with (53), these data demonstrate that additional compounds can be made using combinations of different types of fungal cells in co-cultures.

Bioconversion of 53 by Immobilized Cells of R. oryzae and C. echinulata var. elegans Alginate beads derived from each fungus (60 g) were distributed over four 500 mL flasks each containing 125 mL sterilized PDB. Steroid 53 (200 mg) in ethanol (5 mL) was added to the flasks. The immobilized cells and substrate were shaken at 180 rpm for five days. After incubation, the aqueous medium was decanted, extracted with ethyl acetate, dried with sodium sulfate, and the solvent was removed in vacuo. The resulting solid (182.4 mg) was purified using column chromatography. Elution with 25% acetone in dichloromethane afforded fed steroid (14.4 mg). Further elution afforded 3β,8,11α,17β-tetrahydroxyandrost-5-ene (91) (3 mg) which resisted crystallization, $[\alpha]_D$+20.8° (c=2.0, CHCl$_3$);

IR: $\nu_{max}$ 3447, 1288 cm$^{-1}$;

HREIMS: m/z (rel. int.) 304.2039 (14) [M-H$_2$O]+ (304.2144 calcd. for C$_{19}$H$_{30}$O$_4$—H$_2$O), 302.1882 (7), 290.2246 (4), 286.1933 (100) [M-2H$_2$O]$^+$;

$^1$H NMR: δ 0.91 (3H, s, H-18), 1.09 (3H, s, H-19), 3.05 (1H, t, J=9.5 Hz, H-3α), 3.67 (1H, m, w/2=18.7 Hz, H-11), 4.23 (1H, m, w/2=9.5 Hz, H-17a), 5.57 (1H, s, H-6);

$^{13}$C NMR: δ 13.6 (CH$_3$-18), 19.2 (CH$_3$-19), 24.2 (CH$_2$-15), 29.2 (CH$_2$-16), 31.2 (CH$_2$-2), 36.0 (CH$_2$-1), 36.7 (CH$_2$-7), 36.9 (CH$_2$-4), 38.7 (C-10), 40.5 (CH-14), 41.6 (CH$_2$-12), 47.8 (CH-9), 53.7 (C-13), 70.6 (CH-3), 71.3 (CH-11), 73.5 (C-8), 82.4 (CH-17), 128.8 (CH-6), 143.7 (C-5).

All the compounds, except one, that were isolated from the co-incubation of C. echinulata and R. oryzae were the same as those from the individual incubations. The novel analog (91), based on $^{13}$C and DEPT NMR spectra, like 90 had a molecular formula of C$_{19}$H$_{30}$O$_4$. This suggested a dihydroxylated derivative of 53. A new methine at δ$_c$ 71.3 was observed along with a nonprotonated carbon at δ 73.5. The $^{13}$C NMR spectrum showed loss of the C-11 methylene and the C-8 methine (20.4, 31.6 ppm respectively). Shifts in the carbon values for C-9 and -12 suggested that both C-8 and -11 had been hydroxylated.

These data demonstrate that filamentous fungi contained in fungal beads can be co-cultured to produce compounds that are not produced by a single species of fungi.

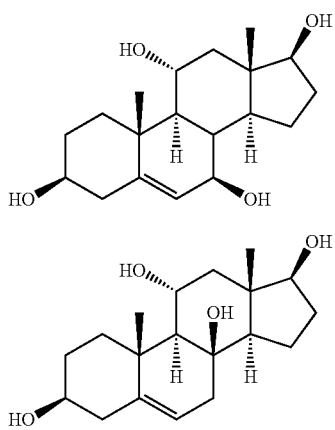

57

58

These data demonstrate that immobilized filamentous fungi can be used for combinatorial biocatalysis. Incubation in an appropriate medium can be used to increase yields of biocatalysis products and to increase the useful life of immobilized cells. Furthermore, incubation of a substrate in the presence of two types of immobilized cells can produce products of crossover, thereby demonstrating the utility of these cells as reusable catalysts and as agents for combinatorial biocatalysis.

Example 6

Additional Mixed Cell Biotransformation Studies

Four species of fungi were used to further investigate the use of multiple species of filamentous fungi in co-fermentations to produce compounds, e.g., for use as compound libraries. The four species used in these experiments were *Rhizopus oryzae* (ATCC 11145), *Mucor plumbeus* ATCC 4740, *Cunninghamella echinulata* var. *elegans* (ATCC 8688a) and *Whetzelinia sclerotiorum* (ATCC 18687). The biocatalysis of the substrates 3β,17β-dihydroxyandrost-5-ene (53) and 17β-hydroxyandrost-4-en-3-one (testosterone) (6) were studied in these experiments.

In general, fungal beads were prepared as described supra and were stored at 4° C. until use in a mixed cell fermentation. For mixed cultures using immobilized fungi, the prepared alginate beads were divided into for equal portions (about 50 mL total, about 25 mL per species of fungus) and placed into four 500 mL erlenmeyer flasks, each containing water (125 mL). The substrate (200 mg) in ethanol (5 mL) was added to the flasks. The flasks were shaken at 180 rpm for five days. After the fermentation was complete the water was decanted from the beads and the former was extracted using ethyl acetate (2×300 mL). The organic solution was dried using sodium sulfate, filtered, and the solvent was removed in vacuo. The residue was analyzed by TLC and purified by column chromatography. The characterization of the some metabolites was aided by their acetylation and further purifications.

Mixed Cell Biotransformations using 3β,17β-DIHYDROXYANDROST-5-ENE (53) as Substrate

*Rhizopus oryzae/Cunninghamella echinulata* var. *elegans*

This fermentation produced one metabolite, 6, that was not found in the individual fungal cell fermentations.

*Rhizopus oryzae/Whetzelinia sclerotiorum*

This fermentation produced one metabolite, 6, that was not found in the individual fungal cell fermentations.

*Rhizopus oryzae/Mucor plumbeus*

This fermentation produced two metabolites that were not found in the previous individual fungal cell incubations: 14α,17β-dihydroxyandrost-4-en-3-one (92) and 7β,17β-dihydroxyandrost-4-en-3-one (93).

*Mucor plumbeus/Cunninghamella echinulata* var. *elegans*

A total of eight new compounds were isolated from this fermentation; 7α,17β-dihydroxyandrost-4-en-3-one (94), 3β,14α,17β-trihydroxyandrost-5-en-7-one (95), 3β,5β,6α,7α,17β-pentahydroxyandrostane (96), 3β,5α,6β,7α,17β-pentahydroxyandrostane (97), 3β,5α,6β,7β,17β-pentahydroxyandrostane (98), 3β,5α,6β,11α,17β-pentahydroxyandrostane (99), 3β,5α,6β,15β,17β-pentahydroxyandrostane (100) and 3β,5α,6β,14α,17β-pentahydroxyandrostane (101).

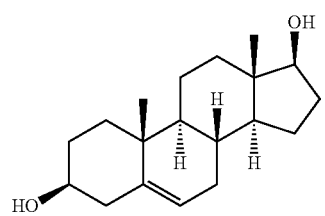

1

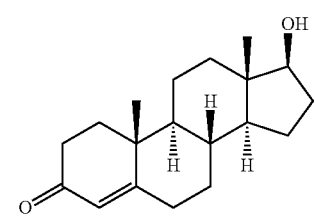

2

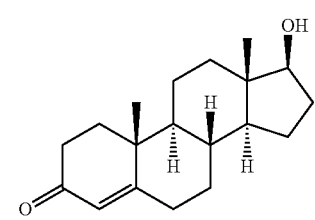

3

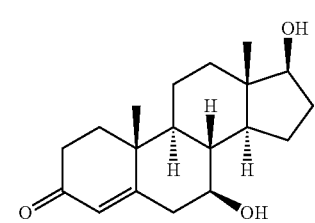

4

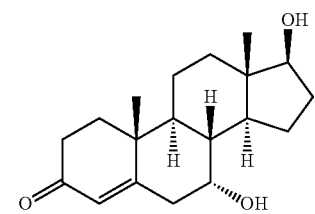

5

-continued

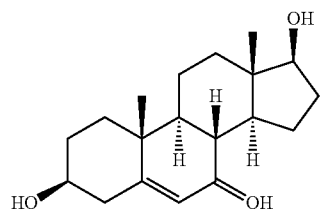
6

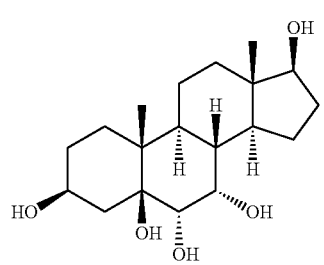
7

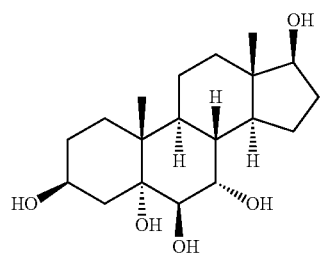
8

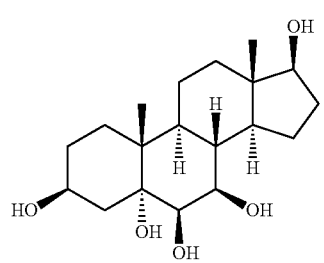
9

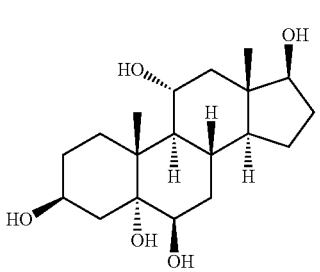
10

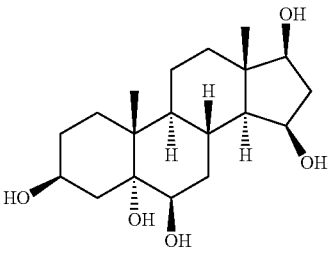
11

-continued

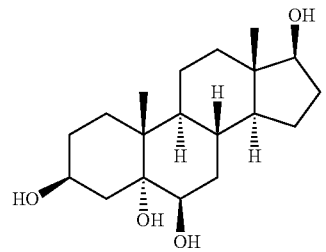
12

Mixed Cell Bioconversion Using 17β-HYDROXYAN-DROST-4-EN-3-ONE (2) as Substrate

*Mucor plumbeus/Rhizopus oryzae*

Fermentations of this experiment yielded 15β,17β-dihydroxyandrost-4-en-3-one (102) in addition to the analogs isolated from the fermentations with the individual fungi.

*Mucor plumbeus/Cunninghamella echinulata* var. *elegans*

This incubation afforded four new products of biotransformation, not found in the fermentations with the original micro-organisms. These were androsta-4,6-diene-3,17-dione (103), 7α-acetoxy-17β-hydroxyandrost-4-en-3-one (104), 7α-hydroxyandrost-4-ene-3,17-dione (105) and 7β,17β-dihydroxyandrost-4-en-3-one (93).

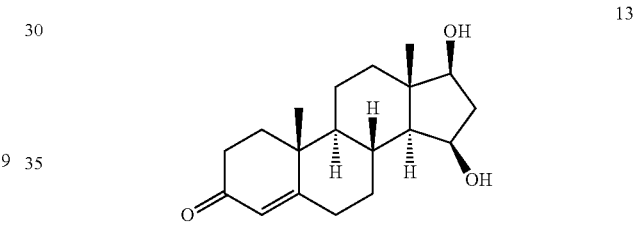
13

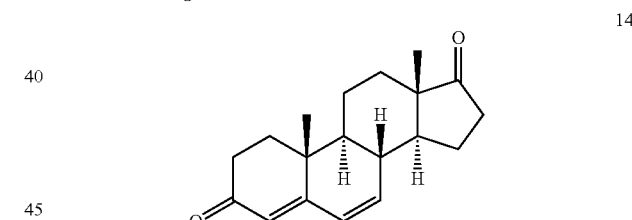
14

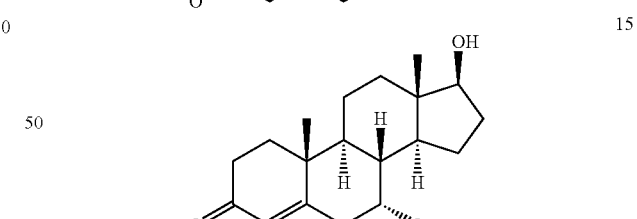
15

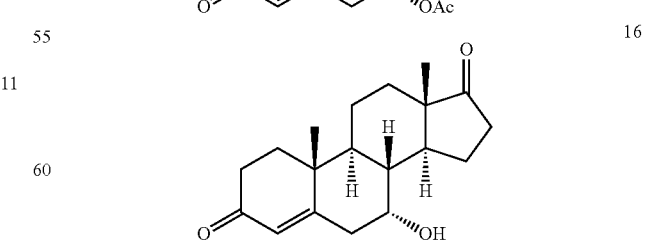
16

Overall, these results described herein demonstrate that macerated fungal mycelium, which is then encapsulated in a matrix such as calcium alginate, retains its biocatalytic activity and can be used in biotransformations. Significantly, the ability of the microorganism to carry out hydroxylation of substrates is preserved.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing a library of bioconversion compounds, the method comprising
providing a first fungal bead containing a grown first fungal species;
providing a second fungal bead containing a grown second fungal species;
combining the first and second fungal beads, a medium free of nutrients that promote fungal growth, and a compound in a single vessel to form an incubation mixture, wherein the first and second fungal species are not growing and are not in contact with each other;
incubating the incubation mixture to produce a library comprising multiple bioconversion compounds; and
isolating a mixture of the multiple bioconversion compounds and screening the isolated mixture of the multiple bioconversion compounds for biological activity without isolating the individual bioconversion compounds.

2. The method of claim 1, wherein the compound is a steroid.

3. The method of claim 1, wherein first or second fungal bead comprises calcium alginate or sodium alginate.

4. The method of claim 1, wherein the first or second fungal species is a filamentous fungus.

5. The method of claim 1, wherein the first or second fungal species is selected from the group consisting of *Rhizopus oryzae, Mucor plumbeus, Cunninghamella echinulata, Aspergillus niger, Phanerochaete chrysosporium,* or *Whetzelinia sclerotiorum.*

6. The method of claim 1, wherein the incubation mixture is incubated for a period between 1 day and 10 days.

7. The method of claim 1, further comprising washing either the first or second fungal bead in distilled water and storing said washed bead in distilled water or buffer at about 4° C.

8. The method of claim 1, wherein the first or second fungal bead is about 3 mm in diameter.

9. The method of claim 1, wherein the compound is

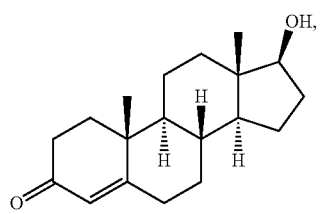

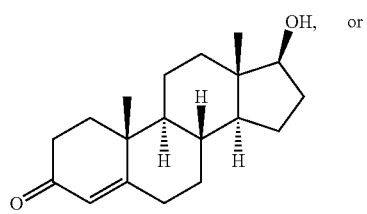

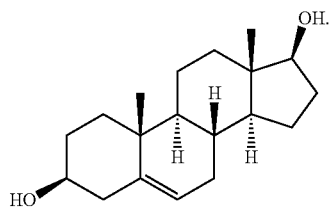

* * * * *